(12) United States Patent
Bootsma

(10) Patent No.: US 9,061,987 B2
(45) Date of Patent: Jun. 23, 2015

(54) OIL COMPOSITION AND METHOD FOR PRODUCING THE SAME

(75) Inventor: Jason Bootsma, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 121 days.

(21) Appl. No.: 12/877,987

(22) Filed: Sep. 8, 2010

(65) Prior Publication Data

US 2011/0086149 A1    Apr. 14, 2011

Related U.S. Application Data

(63) Continuation-in-part of application No. 12/208,127, filed on Sep. 10, 2008, now Pat. No. 8,702,819.

(60) Provisional application No. 61/241,874, filed on Sep. 12, 2009.

(51) Int. Cl.
*A23C 15/14* (2006.01)
*A23D 7/00* (2006.01)
(Continued)

(52) U.S. Cl.
CPC . *C07C 57/12* (2013.01); *A23D 9/00* (2013.01); *A23D 9/007* (2013.01); *A23D 9/02* (2013.01); *C10L 1/026* (2013.01); *C11B 5/0007* (2013.01); *C11B 5/0092* (2013.01); *C11B 13/00* (2013.01); *C11C 1/005* (2013.01); *C11C 1/045* (2013.01); *C11C 1/08* (2013.01); *C11C 3/00* (2013.01); *C07C 53/00* (2013.01); *Y02E 50/13* (2013.01)

(58) Field of Classification Search
CPC ........... A23D 9/00; A23D 9/007; A23D 9/02; C07C 53/00; C07C 57/12; C07C 1/005; C07C 1/045; C07C 1/08; C07C 3/00; C10L 1/026; C11B 13/00; C11B 5/0007; C11B 5/0092; C11B 1/00; C11B 1/04; C11C 1/005; C11C 1/045; C11C 1/08; C11C 3/00; Y02E 50/13; Y02E 50/17; Y02E 50/16; C12P 7/10; C12P 7/06; C12P 7/08; F23C 2900/07002; F23D 14/24; B63B 1/047; A23J 1/006; B01D 3/14; C07K 1/34; C07K 1/36
USPC ...................... 426/18, 31, 541, 601, 417, 627
See application file for complete search history.

(56) References Cited

U.S. PATENT DOCUMENTS

| 4,284,652 A | 8/1981 | Christensen |
| 4,341,713 A * | 7/1982 | Stolp et al. ....................... 554/17 |

(Continued)

FOREIGN PATENT DOCUMENTS

| CA | 1230546 | 12/1987 |
| EP | 0082581 | 6/1983 |

(Continued)

OTHER PUBLICATIONS

Bromberg, "Blends and Semiinterpenetrating Networks of Zein and Poly(N,N-dimethylacrylamide)," J. Phys. Chem., vol. 100, No. 32, pp. 13811-13814 (1996).

(Continued)

*Primary Examiner* — James Goloboy
*Assistant Examiner* — Latosha Hines
(74) *Attorney, Agent, or Firm* — Foley & Lardner LLP

(57) ABSTRACT

This invention relates to a corn oil composition comprising unrefined corn oil having a free fatty acid content of less than about 5 weight percent, and methods for producing the same.

22 Claims, 18 Drawing Sheets

(51) Int. Cl.
| | |
|---|---|
| *A23D 9/00* | (2006.01) |
| *C07C 57/12* | (2006.01) |
| *A23D 9/007* | (2006.01) |
| *A23D 9/02* | (2006.01) |
| *C10L 1/02* | (2006.01) |
| *C11B 5/00* | (2006.01) |
| *C11B 13/00* | (2006.01) |
| *C11C 1/00* | (2006.01) |
| *C11C 1/04* | (2006.01) |
| *C11C 1/08* | (2006.01) |
| *C11C 3/00* | (2006.01) |
| *C07C 53/00* | (2006.01) |

(56) References Cited

U.S. PATENT DOCUMENTS

| | | | |
|---|---|---|---|
| 4,466,889 A | 8/1984 | Miller et al. | |
| 4,721,706 A | 1/1988 | Bessler et al. | |
| 5,397,834 A | 3/1995 | Jane et al. | |
| 5,406,768 A | 4/1995 | Giuseppe et al. | |
| 5,441,801 A | 8/1995 | Deaner et al. | |
| 5,486,553 A | 1/1996 | Deaner et al. | |
| 5,497,594 A | 3/1996 | Giuseppe et al. | |
| 5,516,472 A | 5/1996 | Laver | |
| 5,518,677 A | 5/1996 | Deaner et al. | |
| 5,539,027 A | 7/1996 | Deaner et al. | |
| 5,578,090 A | 11/1996 | Bradin | |
| 5,596,080 A | 1/1997 | Pelosi | |
| 5,635,123 A | 6/1997 | Riebel et al. | |
| 5,725,939 A | 3/1998 | Nishibori | |
| 5,739,015 A | 4/1998 | Srinivasan | |
| 5,746,958 A | 5/1998 | Gustafsson et al. | |
| 5,851,469 A | 12/1998 | Muller et al. | |
| 5,914,367 A | 6/1999 | Dordick et al. | |
| 5,948,524 A | 9/1999 | Seethamraju et al. | |
| 6,054,207 A | 4/2000 | Finley | |
| 6,122,877 A | 9/2000 | Hendrickson et al. | |
| 6,313,105 B1 | 11/2001 | Bengs et al. | |
| 6,323,265 B1 | 11/2001 | Bengs et al. | |
| 6,527,532 B1 | 3/2003 | Muller et al. | |
| 6,593,625 B2 | 7/2003 | Christiansen et al. | |
| 6,648,930 B2 | 11/2003 | Ulrich et al. | |
| 6,703,227 B2 | 3/2004 | Jakel et al. | |
| 7,214,414 B2 | 5/2007 | Khemani et al. | |
| 7,601,858 B2 | 10/2009 | Cantrell et al. | |
| 7,638,644 B2 | 12/2009 | Lee et al. | |
| 2003/0180415 A1* | 9/2003 | Stiefel et al. | 426/18 |
| 2003/0180897 A1* | 9/2003 | Ulrich et al. | 435/134 |
| 2004/0022881 A1 | 2/2004 | Hauptmann et al. | |
| 2004/0234649 A1* | 11/2004 | Lewis et al. | 426/31 |
| 2004/0241254 A1 | 12/2004 | Kopas et al. | |
| 2005/0019545 A1 | 1/2005 | Riebel | |
| 2005/0101700 A1 | 5/2005 | Riebel | |
| 2006/0041153 A1 | 2/2006 | Cantrell et al. | |
| 2007/0238891 A1* | 10/2007 | Winsness et al. | 554/8 |
| 2007/0244719 A1* | 10/2007 | David | 705/2 |
| 2010/0058649 A1 | 3/2010 | Bootsma | |

FOREIGN PATENT DOCUMENTS

| | | |
|---|---|---|
| GB | 1247473 | 9/1971 |
| WO | WO-03/016441 | 2/2003 |
| WO | WO 2004/057008 | 7/2004 |
| WO | WO-2004/081193 | 9/2004 |
| WO | WO 2004/113435 | 12/2004 |
| WO | WO-2008/039859 | 4/2008 |
| WO | WO 2008/082106 | 7/2008 |

OTHER PUBLICATIONS

Demirci et al., "Repeated-batch fermentation in biofilm reactors with plastic-composite supports for lactic acid production," Appl. Microbiol. Biotechnol., vol. 43, pp. 585-589 (1995).

Ikada et al., "Grafting of Proteins Onto Polymer Surfaces with the Use of Oxidized Starch," J. Biomed. Mater. Res., 13(4):607-22 (1979).

Kunduru et al., "Continuous ethanol production by *Zymomonas mobilis* and *Saccharomyces cerevisiae* in biofilm reactors," Journal of Industrial Microbiology, vol. 16, pp. 249-256 (1996).

Shewry et al., "The Prolamin Storage Proteins of Sorghum and Millets," Rothamsted Research, Harpenden. Herts AL5 27Q, UK, Date Unknown.

Shin et al., "Preparation of Plastic and Biopolymer Multilayer Films by Plasma Source Ion Implementation," J. Agric. Food Chem., vol. 50, No. 16, pp. 4608-4614 (2002).

Wu et al., "Chemical modification of zein by bifunctional polycaprolactone (PCL)," Polymer, vol. 44, pp. 3909-3919 (2003).

Wu et al., "Studies on the toughness and water resistance of zein-based polymers by modification," Polymer, vol. 44, pp. 3901-3908 (2003).

Yamada et al., "Improved water resistance in edible zein films and composites for biodegradable food packaging," International Journal of Food Science and Technology, vol. 30, pp. 599-608 (1995).

PCT International Preliminary Report on Patentability dated Mar. 21, 2013 in related PCT Patent Application No. PCT/US2011/050705.

Blanch et al., "Comprimidos de Accion Sostenida de Matriz Plastica," IT Farmaco—Ed. Pr., 1968, 23(4):182-194.

Moreau et al., "The Composition of Crude Corn Oil Recovered after Fermentation via Centrifugation from a Commercial Dry Grind Ethanol Process", Journal of the American Oil Chemists' Society, 2010, 87(8):895-902.

Winkler-Moser et al., "Antioxidant Activity of Phytochemicals from Distillers Dried Grain Oil", Journal of the American Oil Chemists' Society, 2009, 86(11):1073-1082.

U.S. Appl. No. 14/139,671, filed Dec. 23, 2013, Bootsma, Jason.

Australian Examination Report for copending AU Patent Appl. No. 2010224336, dated Jan. 29, 2014.

* cited by examiner

OIL COMPOSITION AND METHOD FOR PRODUCING THE SAME

CROSS REFERENCE TO RELATED APPLICATIONS

This Application claims priority to U.S. Provisional Application Ser. No. 61/241,874, filed Sep. 12, 2009, and is a continuation-in-part of U.S. patent application Ser. No. 12/208,127, filed Sep. 10, 2008, both of which are incorporated herein by reference in their entirety.

FIELD

This invention relates to corn oil compositions and, in particular, corn oil compositions containing a free fatty acid content of less than 5 weight percent as well as to methods for producing the same.

BACKGROUND

Ethanol can be produced from grain-based feedstocks (e.g., corn, sorghum/milo, barley, wheat, soybeans, etc.), from sugar (e.g., sugar cane, sugar beets, etc.), or from biomass (e.g., lignocellulosic feedstocks, such as switchgrass, corn cobs and stover, wood, or other plant material).

In a conventional ethanol plant, corn is used as a feedstock and ethanol is produced from starch contained within the corn. Corn kernels are cleaned and milled to prepare starch-containing material for processing. Corn kernels can also be fractionated to separate the starch-containing material (e.g., endosperm) from other matter (such as fiber and germ). The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which can be dried into dried distillers grains (DDG) and sold, for example, as an animal feed product). Other co-products (e.g., syrup and oil contained in the syrup), can also be recovered from the whole stillage. Water removed from the fermentation product in distillation can be treated for re-use at the plant.

Various processes for recovering oil from a fermentation product are currently known in the art. Such processes, however, can be expensive, inefficient or even dangerous. For example, some process, such as that set forth in WO 2008/039859, utilize a solvent extraction technique that, in turn, requires the use of volatile organic compounds such as hexane. Other processes, such as that set forth in U.S. Application Publication No. 2007/0238891, utilize high amounts of heat. Still other conventional processes, such as that set forth in U.S. Application Publication No. 2006/0041152 and 2006/0041153, simply apply a centrifugal force to a fermented product in an attempt to separate an oil product.

Conventional processes for recovering oil from a fermentation product can sacrifice oil quality such that the oil contains a high level of free fatty acids. The presence of a high level of free fatty acids can hamper the production of end products such as, for example, the yield and quality of any bio-diesel eventually produced with the oil as a feedstock. Processes for producing ethanol, such as the process set forth in WO 2004/081193, produce fermentation byproducts which contain increased levels of oils while maintaining a low level of free fatty acids. However, upon application of a centrifugal force to the fermented product, an emulsion can form which effectively locks the valuable oil within the emulsion. Thus, a problem exists in that both conventional and novel processes, alike, cannot effectively, efficiently or safely separate or "break" quality oil from a fermented product.

SUMMARY OF THE INVENTION

This invention relates to a corn oil composition comprising unrefined corn oil having a free fatty acid content of less than about 5 weight percent; a moisture content of from about 0.2 to about 1 weight percent; and an alkali metal ion and/or alkaline metal ion content of greater than 10 ppm.

This invention also relates to a method for providing a corn oil composition from a corn fermentation residue comprising the steps of a) separating the corn fermentation residue to provide an emulsion layer and a first aqueous layer; b) adjusting the pH of the emulsion layer to provide a corn oil layer and a second aqueous layer; and c) separating the corn oil layer from the second aqueous layer to provide the corn oil composition. This invention further relates to a distillers dried grain comprising about 4% or less fat.

DETAILED DESCRIPTION OF THE INVENTION

Figure 1A:
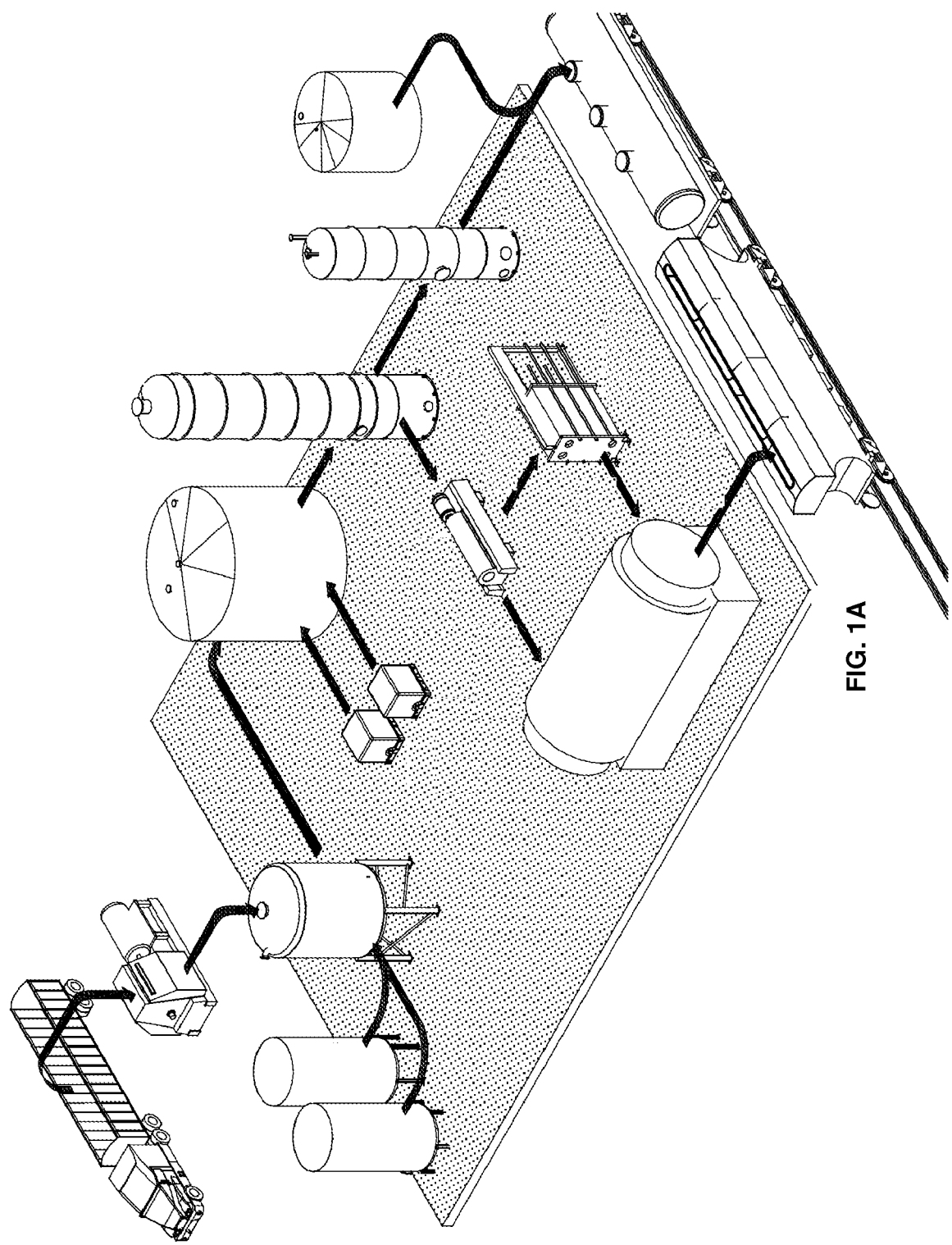
FIG. 1A is a perspective view of a biorefinery comprising a cellulosic ethanol production facility.
Figure 1B:
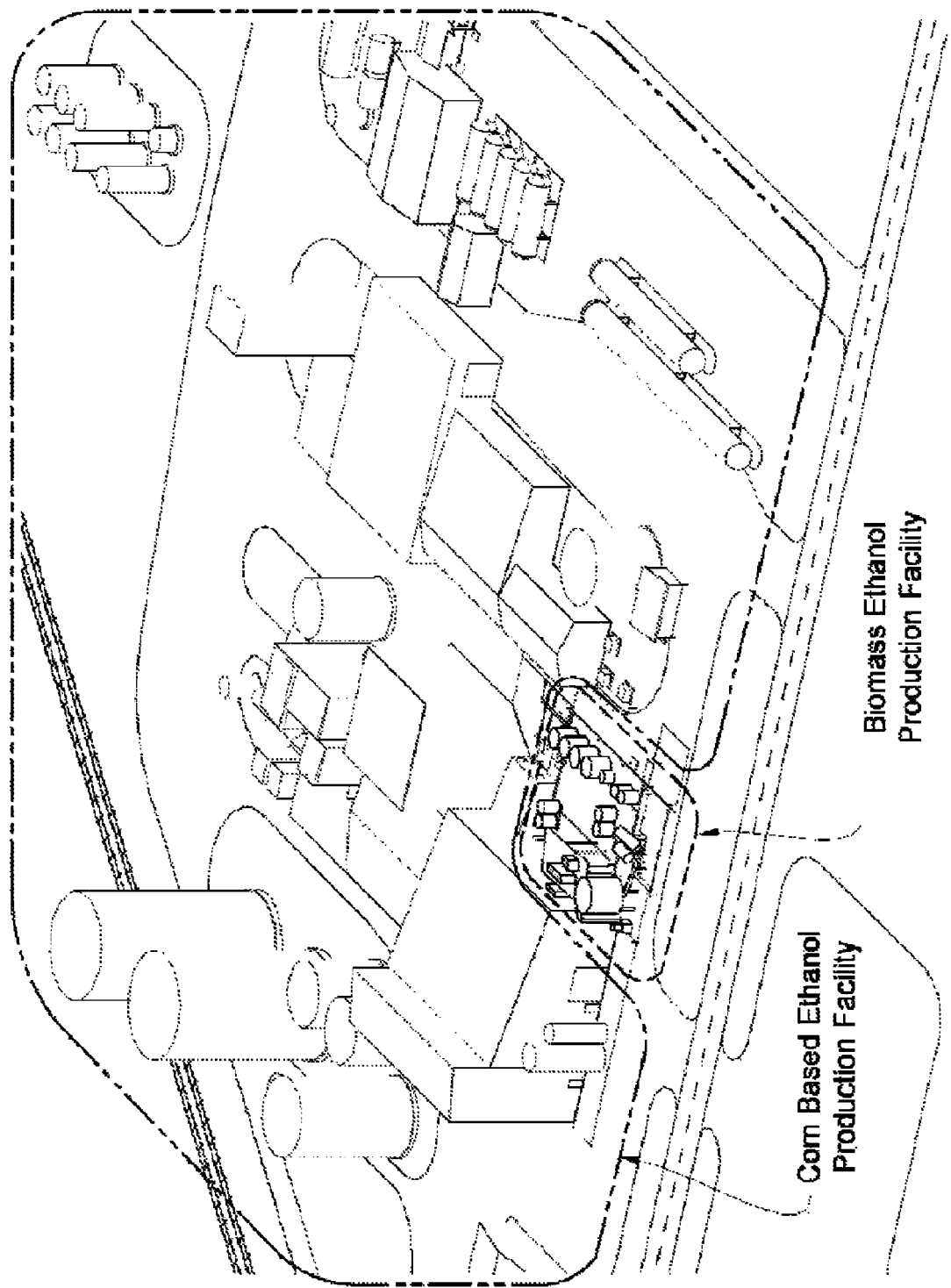
FIG. 1B is a perspective view of a biorefinery comprising a cellulosic ethanol production facility and a corn-based ethanol production facility.

This invention relates to a corn oil composition and a method for producing the same.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

It must be noted that as used herein and in the appended claims, the singular forms "a", "an", and "the" include plural referents unless the context clearly dictates otherwise. Thus, for example, reference to "an alkali metal ion" includes a plurality of alkali metal ions.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of shall mean excluding more than trace elements of other ingredients and substantial method steps. Embodiments defined by each of these transition terms are within the scope of this invention.

As used herein, the term "about" when used before a numerical designation, e.g., temperature, time, amount, and concentration, including range, indicates approximations which may vary by (+) or (−) 10%, 5% or 1%.

As used herein, the term "unrefined corn oil" refers to corn oil which has not been subjected to a refining process, such as alkali refining or physical refining (i.e., distillation, deodorization, bleaching, etc.).

As used herein, the term "free fatty acid" refers to an unesterified fatty acid, or more specifically, a fatty acid having a carboxylic acid head and a saturated or unsaturated unbranched aliphatic tail (group) of from 4 to 28 carbons. The term "aliphatic" has it generally recognized meaning and refers to a group containing only carbon and hydrogen atoms which is straight chain, branched chain, cyclic, saturated or unsaturated but not aromatic.

As used herein, the term "moisture content" refers to the amount of water and other soluble components in the oil composition. The moisture in the corn oil composition contains the alkali and/or alkaline metal, and may contain other soluble components, such as volatile material including hexane, ethanol, methanol, and the like.

As used herein, the term "an alkali metal ion" refers to one or more metal ion of Group 1 of the periodic table (e.g. lithium ($L^+$), sodium ($Na^+$), potassium ($K^+$), etc.).

As used herein, the term "an alkaline metal ion" refers to a metal ion of Group 2 of the periodic table (e.g. magnesium ($Mg^{2+}$), calcium ($Ca^{2+}$), etc.).

As used herein, the term "insoluble" refers to material in the oil which is not solvated by the aqueous portion, the oil or the moisture content within the oil.

As used herein, the term "unsaponifiables" refers to components of the oil that do not form soaps when blended with a base, and includes any variety of possible non-triglyceride materials. This material can act as contaminants during biodiesel production. Unsaponifiable material can significantly reduce the end product yields of the oil composition and can, in turn, reduce end product yields of the methods disclosed herein.

As used herein, the term "peroxide value" refers to the amount of peroxide oxygen (in millimoles) per 1 kilogram of fat or oil and is a test of the oxidation of the double bonds of the oils. The peroxide value is determined by measuring the amount of iodine ($I^-$) via colorimetry which is formed by the reaction of peroxides (ROOH) formed in the oil with iodide via the following equation: $2\ I^- + H_2O + ROOH \rightarrow ROH + 2OH^- + I_2$.

As used herein, the term "oxidative stability index value" refers to the length of time the oil resists oxidation at a given temperature. Typically, the oxidation of oil is slow, until the natural resistance (due to the degree of saturation, natural or added antioxidants, etc.) is overcome, at which point oxidation accelerates and becomes very rapid. The measurement of this time is the oxidative stability index value.

As used herein, the term "corn fermentation residue" refers to the residual components of a corn fermentation process after the ethanol has been recovered, typically via distillation. Typically, the corn fermentation residue comprises water, any residual starch, enzymes, etc.

As used herein, the term "syrup" refers to the viscous composition which is provided by the evaporation of the thin stillage.

As used herein, the term "base" refers to a compound or composition which raises the pH of an aqueous solution. Suitable bases for use in this invention include, but are not limited to, sodium hydroxide, potassium hydroxide, calcium hydroxide, or spent alkali wash solution.

As used herein, the term "alkali wash solution" refers to the basic solution which is used to disinfect the fermentor after the fermentation process has been completed. The alkali wash solution typically comprises sodium hydroxide.

2. Embodiments

This invention generally relates to oil compositions recovered from a fermentation byproduct. The oil compositions contain low levels of free fatty acids making them valuable for use in bio-diesel, edible and nutraceutical applications. This invention also relates to methods of recovering such oil compositions from a fermentation process.

Figure 2:
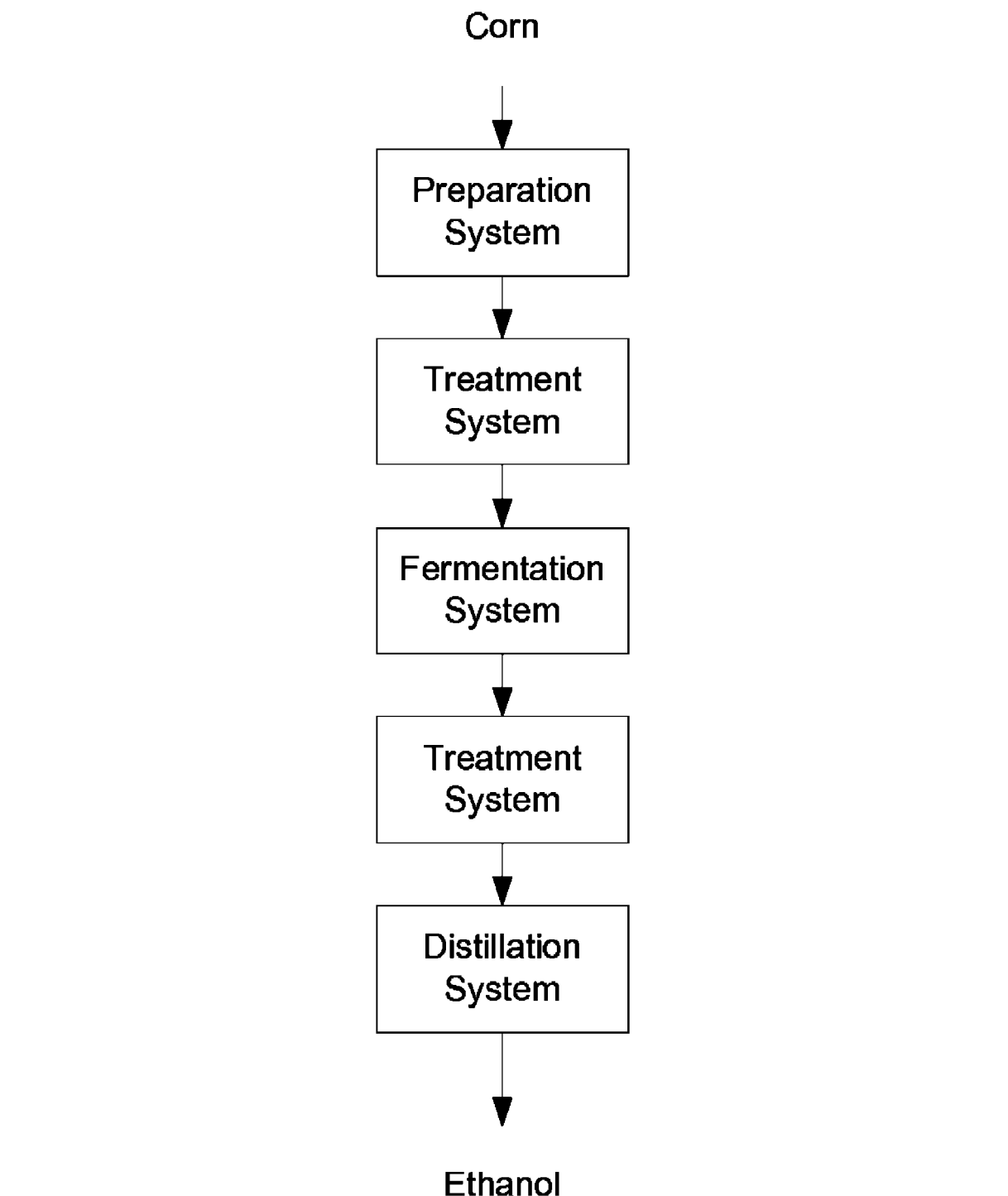
FIG. 2 is a schematic block flow diagram of a process for producing ethanol from corn.
Figure 3:
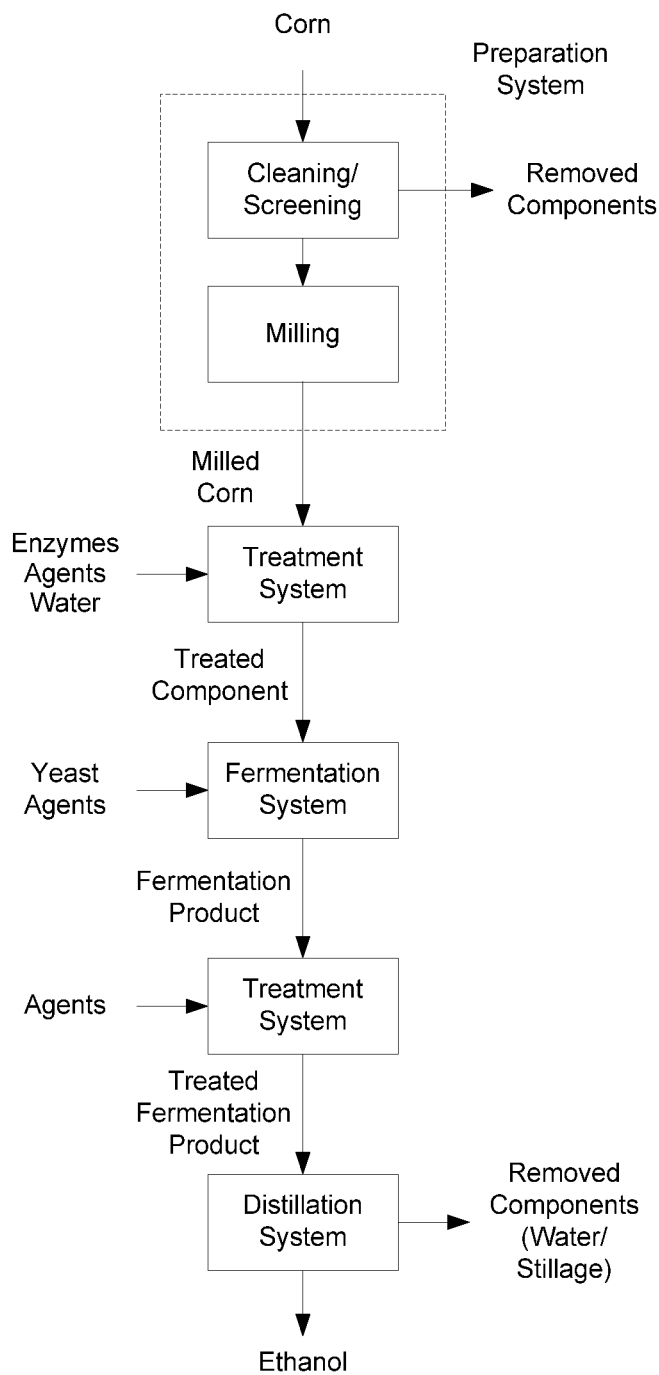
FIG. 3 is a schematic flow diagram of a process for producing ethanol from corn.

The corn oil of this invention is provided by the fermentation of corn in the production of ethanol. Referring to FIGS. 2 and 3, in a typical exemplary ethanol production process, corn can be prepared for further treatment in a preparation system. As seen in FIG. 3, the preparation system may comprise a cleaning or screening step to remove foreign material, such as rocks, dirt, sand, pieces of corn cobs and stalk, and other unfermentable material. After cleaning/screening, the particle size of corn can be reduced by milling to facilitate further processing. The corn kernels may also be fractionated into starch-containing endosperm and fiber and germ. The milled corn or endosperm is then slurried with water, enzymes and agents to facilitate the conversion of starch into sugar (e.g. glucose). The sugar can then be converted into ethanol by an ethanologen (e.g. yeast) in a fermentation system. In one embodiment, the fermentation is carried out without creating a hot slurry (i.e., without cooking). In such an embodiment, the fermentation includes the step of saccharifying the starch composition with an enzyme composition to form a saccharified composition (e.g., without cooking). In one embodiment the starch composition comprises water and from 5% to 60% dried solids granular starch, based on the total weight of the starch composition. In another embodiment, the starch composition comprises 10% to 50% dried solids granular starch, or 15% to 40% dried solids granular starch, or 20% to 25% dried solids granular starch, based on the total weight of the starch composition.

The fermentation product is beer, which comprises ethanol, water, oil, additional soluble components, unfermented particulate matter, etc. The fermentation product can then be distilled to provide ethanol, leaving the remaining components as whole stillage. The whole stillage can then be separated to provide a liquid component (i.e. thin stillage) and a solid component. The solid component can be dried to provide the distillers dried grain of this invention, whereas the thin stillage can be taken on to provide the oil compositions of this invention.

Corn Oil Compositions

One aspect of this invention provides an unrefined corn oil composition comprising having a free fatty acid content of less than about 5 weight percent; a moisture content of from about 0.2 to about 1 weight percent; and an alkali metal ion and/or alkaline metal ion content of greater than 10 ppm. The unrefined corn oil of this invention has not been subjected to a refining process. Such refining processes include alkali refining and/or physical refining (i.e., distillation, deodorization, bleaching, etc.), and are used to lower the free fatty acid content, the moisture content, the insoluble content and/or the unsaponifiables content.

The free fatty acid content of the present unrefined corn oil composition is less than about 5 weight percent. The oil composition described herein has a free fatty acid content level that can reduce the amount of front-end refining or processing for use in bio-diesel production. The fuel properties of bio-diesel are determined by the amounts of each fatty acid in the feedstock used to produce the fatty acid methyl esters. In some embodiments, the free fatty acid content comprises at least one fatty acid selected from the group consisting of $C_{16}$ palmitic, $C_{18}$ stearic, $C_{18-1}$ oleic, $C_{18-2}$ linoleic, and $C_{18-3}$ linolenic (where the number after the "–" reflects the number of sites of unsaturation). In some embodiments, the free fatty acid content is less than 5 weight percent. For example, in some embodiments, the free fatty acid content is less than about 4 weight percent, or alternatively, less than about 3 weight percent, or alternatively, less than about 2 weight percent, or alternatively, less than about 1 weight percent.

Maintaining low levels of moisture is advantageous as moisture can result in the formation of free fatty acids. The unrefined corn oil composition of this invention has a moisture content of less than about 1 weight percent. The moisture in the present corn oil composition can comprise water along with other soluble components, such as one or more alkali and/or alkaline metal, and may further contain other soluble components, such as volatile material including hexane, ethanol, methanol, and the like. The pH of the water that makes up the moisture content is, in general, alkaline (i.e., >7) and comprises the one or more alkali and/or alkaline metals. In some embodiments, the moisture content of the unrefined corn oil composition is from about 0.2 to about 1 weight percent, or alternatively, about or less than about 0.8 weight percent, or alternatively, about or less than about 0.6 weight percent, or alternatively, about or less than about 0.4 weight percent, or alternatively, about 0.2 weight percent. In certain embodiments, the metal ion concentration of the moisture content is about 2,000 ppm. Accordingly, an unrefined corn oil composition having from about 0.2 to about 1 weight percent would have a metal ion concentration of from about 4 ppm to about 20 ppm. Typically, the moisture content of the unrefined corn oil composition is about 0.5 weight percent having a metal ion concentration of about 2000 ppm, resulting in an ion concentration in the oil composition of about 10 ppm. In some embodiments, the unrefined corn oil composition has a metal ion concentration of greater than about 0.4 ppm, or greater than about 0.5 ppm, or greater than about 0.6 ppm, or greater than about 0.7 ppm, or greater than about 0.8 ppm, or 20 ppm.

As is stated above, the moisture content is, in general, alkaline (i.e., >7). Accordingly, the water content in the oil comprises an alkali metal ion and/or alkaline metal ion content of or greater than about 10 ppm. The alkali metal ion present in the composition can be any alkali metal ion and/or any alkaline metal ion, and is in some embodiments, any combination of lithium ($Li^+$), sodium ($Na^+$), magnesium ($Mg^{2+}$), potassium ($K^+$) and/or calcium ($Ca^{2+}$).

In some embodiments, the alkaline moisture content can comprise an organic base, such as ammonia and/or ammonium ions. Accordingly, in one embodiment, this invention is directed to an unrefined corn oil composition comprising having a free fatty acid content of less than about 5 weight percent; a moisture content of from about 0.2 to about 1 weight percent; and an ammonia and/or ammonium ion content of greater than about10 ppm, or from about 4 ppm to about 20 ppm.

In some embodiments, the unrefined corn oil has an insoluble content of less than about 1 weight percent. The insoluble content is not solvated by the aqueous portion, the oil or the moisture within the oil, and can include material such as residual solid (e.g. corn fiber).

In some embodiments, the unrefined corn oil has an unsaponifiables content less than about 3 weight percent, or less than about 2 weight percent, or less than about 1 weight percent. Unsaponifiable matter can significantly reduce the end product yields of the oil composition and can, in turn, reduce end product yields of the methods disclosed herein. The unsaponifiables content of the oil does not form soaps when blended with a base, and includes any variety of possible non-triglyceride materials that act as contaminants during biodiesel production.

The unrefined corn oil of this invention can further comprise various other oil soluble components. It is contemplated that the amount of such components would not be so much that the unrefined corn oil composition would require refining prior to being used as a biodiesel, for example. Such components can include, for example, one or more of lutein, cis-lutein, zeaxanthin, alpha-cryptoxanthin, beta-cryptoxanthin, alpha-carotene, beta-carotene, cis-beta-carotene, alpha-tocopherol, beta-tocopherol, delta-tocopherol, or gamma-tocopherol, alpha-tocotrienol, beta-tocotrienol, gamma-tocotrienol, and/or delta-tocotrienol. In some embodiments, the unrefined corn oil composition has a tocopherol content less than about 1 mg/g. In some embodiments, the unrefined corn oil composition has a tocotrienol content less than about 1.3 mg/g. In some embodiments, the unrefined corn oil composition has a beta-carotene content greater than about 2 μg/g. Such components are known antioxidants and can thus provide an oxidative stability to the unrefined corn oil composition.

The unrefined corn oil composition of this invention exhibits a high level of oxidative stability than corn oils prepared via conventional methods. This can be due to any combination of factors, such as, the degree of saturation of the oil, the natural antioxidants, and the like, and can easily be determined using methods well known in the art. In some embodiments, the oxidative stability of the unrefined corn oil composition is greater than about 4 hours at a temperature of about 110° C. (See Example 4). Further, the oxidative stability can be assessed using its peroxide value. In some embodiments, the unrefined corn oil composition exhibits a peroxide value of less than about 2 parts per million, or less than 1 part per million.

Methods

One aspect of this invention is directed to a method for providing a corn oil composition from a corn fermentation residue comprising the steps of:
b) adjusting the pH of the corn fermentation residue to provide a corn oil layer and an aqueous layer; and
c) separating the corn oil layer from the aqueous layer to provide the corn oil composition.

One aspect of this invention is directed to a method for providing a corn oil composition from a corn fermentation residue comprising the steps of:
a) separating the corn fermentation residue to provide an emulsion layer and a first aqueous layer;
b) adjusting the pH of the emulsion layer to provide a corn oil layer and a second aqueous layer; and
c) separating the corn oil layer from the second aqueous layer to provide the corn oil composition.

Figure 4A:
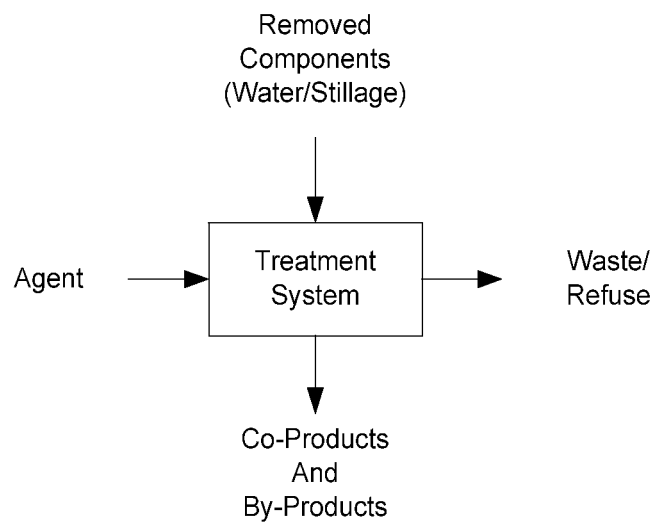
FIG. 4A shows the removed components (e.g., whole stillage), which comprise water, soluble components, oil and unfermented solids (e.g., the solids component of the beer with substantially all ethanol removed), can be dried into distillers dried grains (DDG) and sold as an animal feed product.

In some embodiments, the corn fermentation residue of this invention comprises whole stillage. In a fermentation process, the whole stillage is the remaining components of the fermentor after the ethanol has been distilled. The whole stillage comprises a solid component and a liquid component. The liquid component of the whole stillage is referred to herein as thin stillage (FIG. 4A). In one embodiment, the whole stillage can be subjected to further processing steps to produce thin stillage. Thin stillage can be recovered from the solid component of the whole stillage by natural phase separation and decanting, or can be accelerated using methods such as centrifugation. In one embodiment, the solid component of the whole stillage can be subjected to drying to provide distillers dried grain and sold as an animal feed product. In some embodiments, the corn fermentation residue comprises thin stillage. In one embodiment, moisture can be removed from the thin stillage to create a concentrated fermented product, herein referred to as syrup. Moisture can be removed in a variety of ways such as, for example, through evaporation under vacuum which, in turn, can prevent fouling. Accordingly, in some embodiments, the corn fermentation residue comprises syrup. In some embodiments, the corn fermentation residue has a moisture content of between about 95% and about 60% weight percent. In some embodiments, the corn fermentation residue has a moisture content of about 95%, or about 90%, or about 85%, or about 80%, or about 75%, or about 70%, or about 65%, or about 60% weight percent.

The method of this invention optionally comprises the step of separating the corn fermentation residue (whole stillage, thin stillage, or syrup) to provide an emulsion layer and a first aqueous layer. The step of separating can be accomplished by simply allowing the phase separation to occur over time and the oil layer decanted or by utilizing centrifuge or a combination thereof, including, but not limited to, for example, a press, extruder, a decanter centrifuge, a disk stack centrifuge, a screen centrifuge or a combination thereof. In some embodiments, the separating does not comprise heating. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

In one embodiment, the resulting emulsion layer contains from about 20% w/w to about 70% w/w oil. In another embodiment, the emulsion layer contains from about 30% w/w to about 60% w/w oil. In yet another embodiment, the emulsion layer contains from about 40% w/w to about 50% w/w oil. The oil fraction may also comprise varying amounts of the overall fermentation residue volume. In one embodiment, the emulsion layer comprises about 20% w/w of the initial fermented product volume.

In one embodiment, the step of separating the corn fermentation residue is performed soon after initial production of the ethanol in order to maintain oil composition quality and prevent exposure to heat and oxygen, which are contributors to the formation of free fatty acids. The emulsion layer, which comprises the oil composition of this invention, is preferably separated from the first aqueous layer. All or a fraction of the first aqueous layer may be further processed or applied to solids such as, for example, distillers dried grain.

In a preferred embodiment, once separated from the first aqueous layer, the pH of the emulsion layer is adjusted such that the emulsion is sufficiently broken, thus providing the oil composition of this invention and a second aqueous layer. The pH adjustment allows selective separation of higher quality oil while leaving the free fatty acids in an aqueous fraction by saponifying the fatty acids thus making them more water soluble. Thus, a portion of the free fatty acid is removed resulting in oil that contains low levels of free fatty acid. The age of the fermented product and the organic acid content of the fermented product can affect the optimum pH for separation, however, the oil fraction is treated with the highest pH possible to reduce the overall free fatty acid content in the separated oil without sacrificing oil quality. Typically, suitable pH's range from about 7.5 to about 10. The mixture of the free oil composition and oil fraction can be removed for further processing.

In another embodiment, the first aqueous layer is not removed from the emulsion layer but rather is subjected to base treatment to form the oil layer and the second aqueous layer which comprises both the first aqueous layer and water resulting from breakage of the emulsion. The oil layer is then separated from the second aqueous layer. Accordingly, in some embodiments, the method comprises the steps of a) adjusting the pH of the corn fermentation residue to provide a corn oil layer and a second aqueous layer; and b) separating the corn oil layer from the second aqueous layer to provide the corn oil composition. In some embodiments, the separating steps do not comprise heating.

In some embodiments, the pH of the emulsion layer is lowered by adding an acid. In one such embodiment, the pH can be adjusted downward by about 1 pH unit, or about 2 pH units, or about 3 pH units. It is contemplated that any inorganic or mineral acid can be used for adjusting the pH of the emulsion layer.

In some embodiments, the pH of the emulsion layer is raised by adding base. In one such embodiment, the pH can be adjusted upward by about 1 pH unit, or about 2 pH units, or about 3 pH units, or about 4 pH units, or about 5 pH units, or about 6 pH units. In some embodiments, the pH of the emulsion layer is less than about 4, or about 3.5, prior to the step of adjusting the pH of the emulsion layer. It is contemplated that any inorganic or mineral base can be used for adjusting the pH of the emulsion layer. Suitable bases include, but are not limited to, a base selected from the group consisting of sodium hydroxide, sodium methoxide, potassium hydroxide, calcium hydroxide, or spent alkali wash solution. In some embodiments, the base can be organic base, such as ammonia. Efficient phase separation of the emulsion layer can be achieved by adjusting the pH of the emulsion layer to about 7.5 to about 10, or from about 8 to about 9, or to a pH of about 8.2.

Figure 5A:
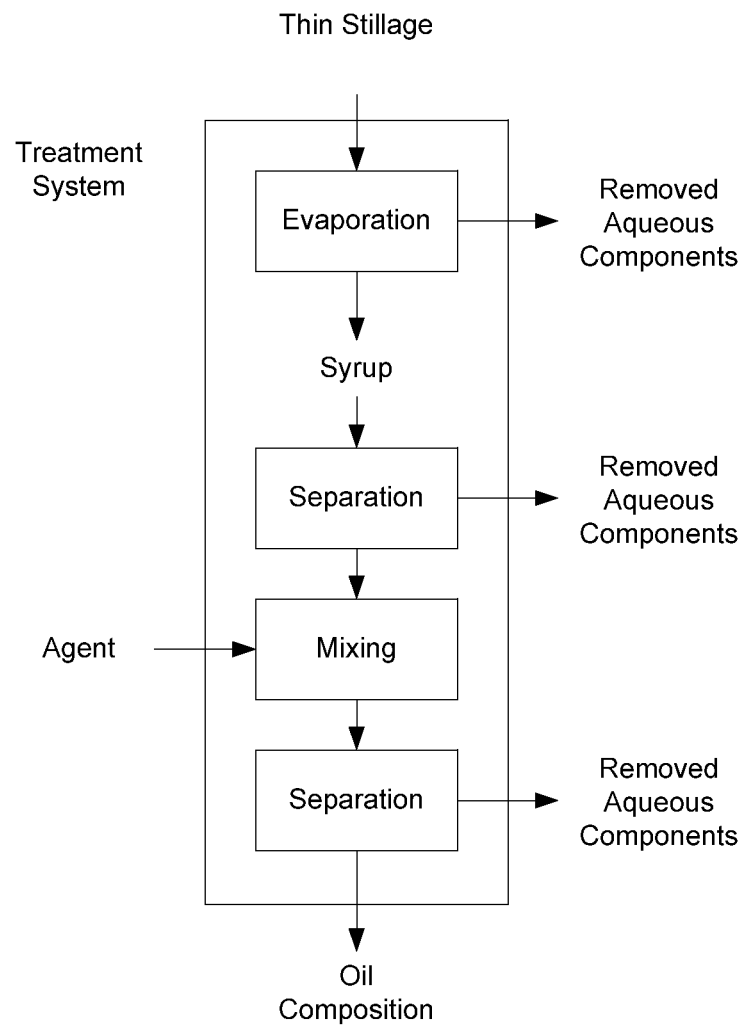
FIGS. 5A and 5B show the second treatment system (i.e. the oil separation system).
Figure 5B:
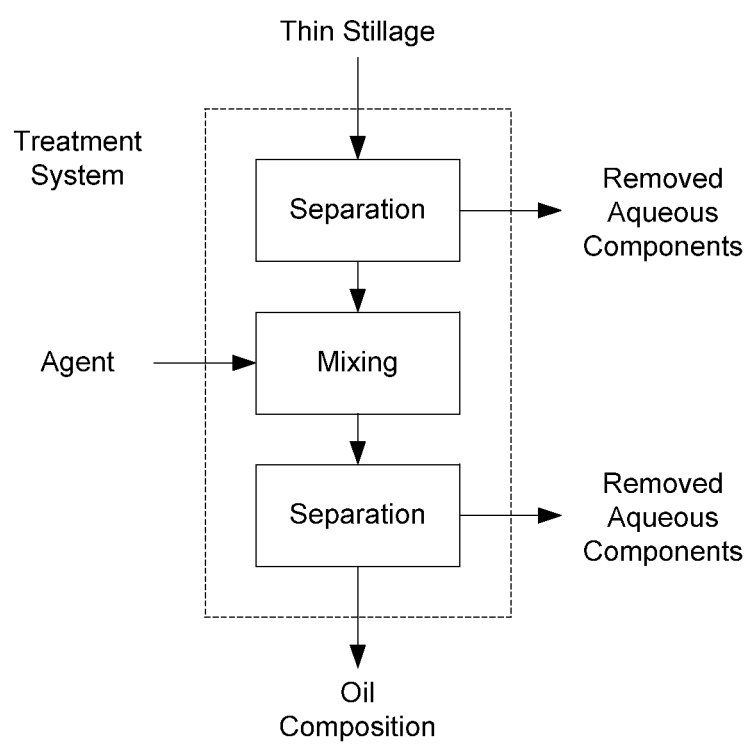

Once the emulsion has sufficiently broken, a corn oil layer and a second aqueous layer are provided (FIGS. 5A and 5B). The corn oil layer comprises the unrefined corn oil as disclosed herein.

In some cases, it may be that an interface layer is present between the oil layer and the aqueous layer, which is known in the art as a rag layer. The interface layer can comprise oil, water, phospholipids, free fatty acids, solids, etc. In some embodiments, the interface layer is substantially removed from the oil layer with the aqueous layer. However, since the interface layer can comprise a significant amount of oil, it may be advantageous to extract the oil from the interface layer. Accordingly, in some embodiments, the interface layer is kept with the oil layer and subjected to the pH adjustment step. The volume of the interface layer can be decreased by about 50% or more by using a greater volume of aqueous solution compared to the volume of the oil layer. Therefore, it may be advantageous to use a greater volume of aqueous solution by adding water and/or using spent alkali wash solution. Such methods may provide an oil having a lower phospholipid concentration.

Figure 6A:
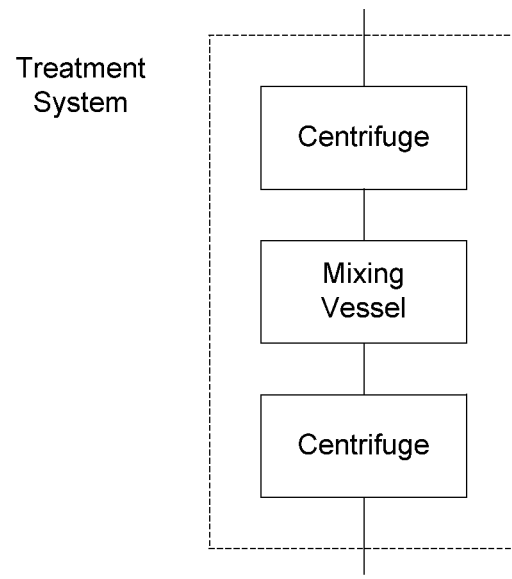
FIGS. 6A and 6B show the treatment system.
Figure 6B:
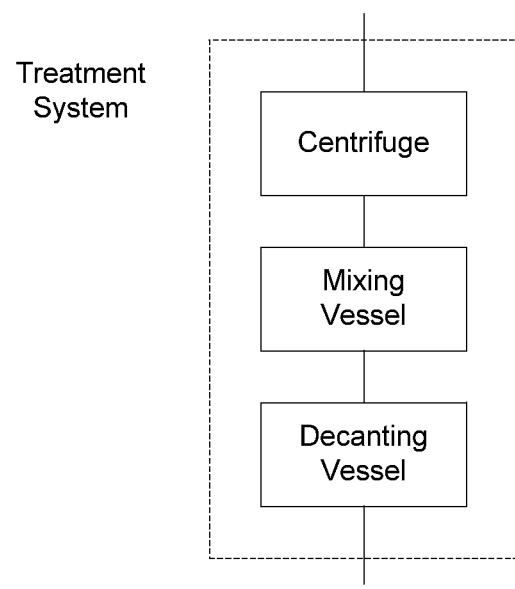

Accordingly, the unrefined corn oil as disclosed herein can be provided by separating the corn oil layer from the second aqueous layer. The step of separating the corn oil layer from the second aqueous layer can be accomplished by simply allowing the phase separation to occur over time and the oil layer decanted or by utilizing centrifuge or a combination thereof, including, but not limited to, for example, a press, extruder, a decanter centrifuge, a disk stack centrifuge, a screen centrifuge or a combination thereof (FIGS. 6A and 6B). In some embodiments, the separating does not comprise heating. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

In one embodiment, the second aqueous portion comprises 60% to 80% moisture, based on the total weight of the second aqueous portion. In one embodiment, the second aqueous portion comprises 10% to 40% protein, based on the total weight of the second aqueous portion. In one embodiment, the second aqueous portion comprises up to 50% oil, based on the total weight of the second aqueous portion. The remainder of the second aqueous portion typically comprises starch, neutral detergent fiber, and the like. The second aqueous portion can be used to treat distillers dried grain or other solids where an increased level of these components is desirable.

Distillers Dried Grains

Figure 4B:
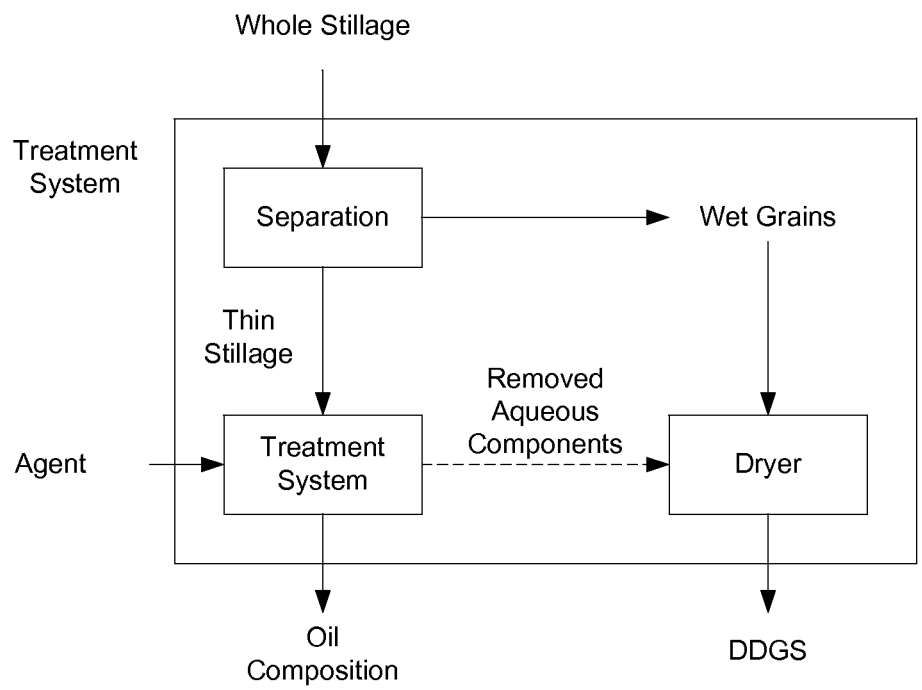
FIG. 4B shows the treatment system which may comprise a separation (to produce thin stillage and wet grains), a second treatment system and a dryer, and produces an oil composition and distillers dried grains plus solubles.

A shown in FIG. 4B, the treatment system may comprise a separation (which produces thin stillage and wet grains), a second treatment system and a dryer, and produces an oil composition and distillers dried grains. The removed aqueous components from the first and/or the second separation steps may be added onto the wet grains in the dryer and dried to provide distillers dried grains with solubles. Accordingly, in one embodiment, this invention provides a distillers dried grain comprising about 4% or less fat, or about 3% or less fat, or about 2% or less fat. In some embodiments, the distillers dried grain further comprises about 20% protein, or about 25% protein, or about 30% protein, about 35% protein, or about 40% protein.

Uses

The oil composition of this invention can be used in a wide variety of applications. Such exemplary applications include the areas of oleochemicals, feed (e.g., animal feed) as well as oils suitable for human consumption, and/or bio-diesel. Accordingly, one embodiment of this invention is a bio-diesel comprising the unrefined corn oil composition as described herein.

Oleochemicals include feedstock chemicals that are suitable for bio-diesel production (fatty acid methyl esters). Industrial oleochemicals are useful in the production of soaps, detergents, wire insulation, industrial lubricants, leather treatments, cutting oils, mining agents for oil well drilling, ink removal, plastic stabilizers, ink and in rubber production. Other industrial applications include waxes, shampoos, personal hygiene and food emulsifier or additive products.

One embodiment of this invention is directed to a distillers dried grain comprising about 4% or less fat. In some embodiments, the distillers dried grain further comprises about 30% protein.

The corn oil of this invention can also be used for human consumption. Products for human consumption include edible oils that meet GRAS crude oil standards, as well as carriers for drug molecules in pharmaceutical preparations. These products fits for human consumption further include nutraceutical applications. The oil compositions described herein contain higher than average levels of various nutraceuticals such as, for example, tocopherols, tocotrienols and phytosterols. In one embodiment and while not intending to be bound to one particular theory, the oil composition's higher than average levels of various nutraceuticals can be attributable to the removal of corn oil directly from the whole kernel as opposed to simply the corn germ itself. The nutraceuticals in the present oil composition may be further processed for inclusion in various applications such as health foods, dietary supplements, food supplements, and food fortification products.

EXAMPLES

A series of examples were conducted according to an exemplary embodiment of the system (as shown in the Figures) in an effort to determine suitable apparatus and operating conditions for the separation of pre-treated biomass.

Example 1

Figure 7:
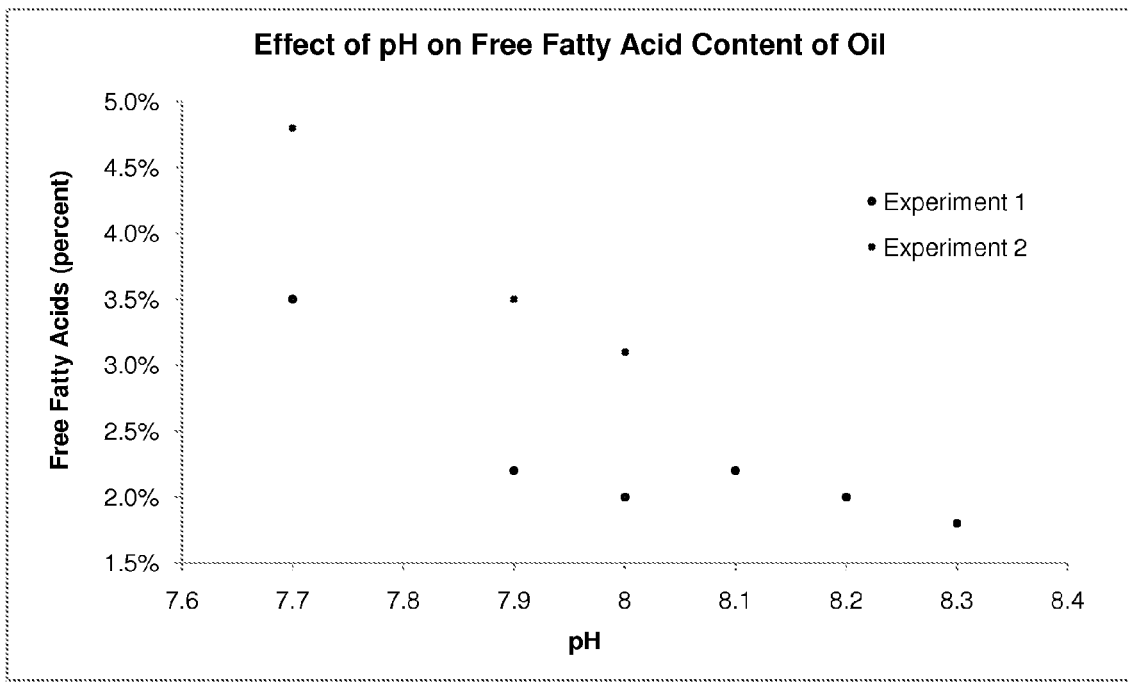
FIG. 7 shows the effect of pH on the fatty acid content of the oil composition.

The pH level capable of providing an oil composition containing a low level of free fatty acid was determined (FIG. 7). First, an oil fraction in the form of an emulsion separated from fermented product was adjusted to the pH levels of 7.7, 7.9, 8.0, 8.1, 8.2, and 8.3. The samples were then centrifuged to separate the oil composition and the oil composition was analyzed for free fatty acid content. This experiment was conducted twice. The results of each experiment, Experiment 1 and Experiment 2, are shown in Table 1.

In summary, those samples tested at lower pH (i.e., below 8.0) exhibited free fatty acid contents above 3.5% w/w while those tested at a pH above 8.1 exhibited a free fatty acid content of below 2% w/w.

TABLE 1

| | pH | | | | | |
|---|---|---|---|---|---|---|
| | 7.7 | 7.9 | 8.0 | 8.1 | 8.2 | 8.3 |
| Free Fatty Acids (percent) Experiment 1 | 3.5 | 2.2 | 2.0 | 2.2 | 2.0 | 1.8 |
| Free Fatty Acids (percent) Experiment 2 | 4.8 | 3.5 | 3.1 | 2.2 | 2.0 | 1.8 |

Example 2

Figure 8:
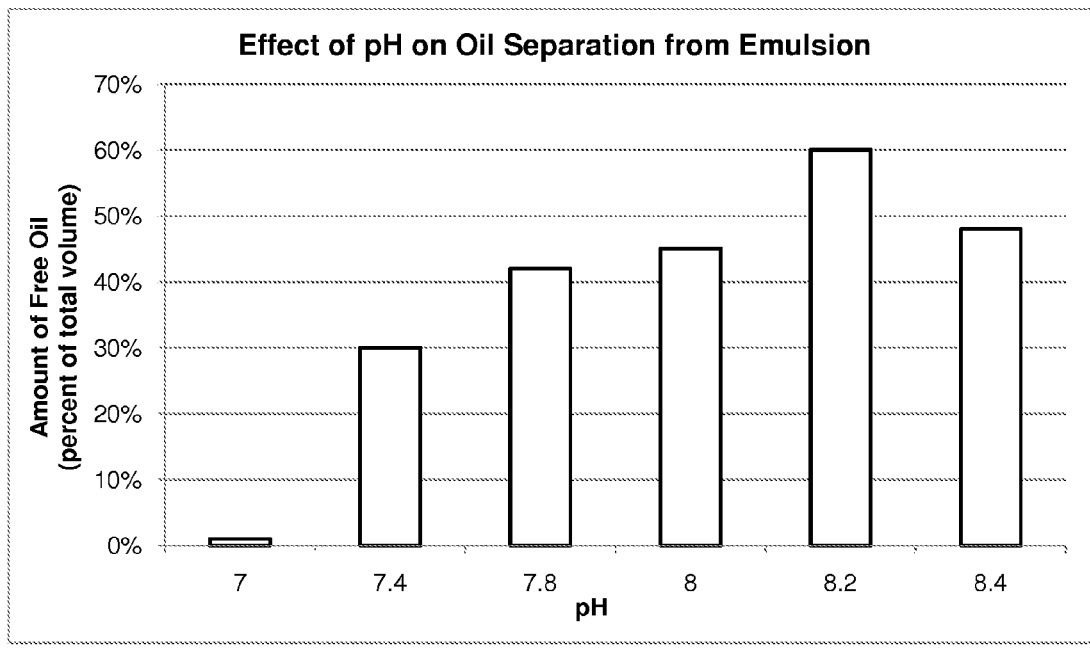
FIG. 8 shows the effect of pH on the oil separation from the emulsion.
Figures 9A, 9B:
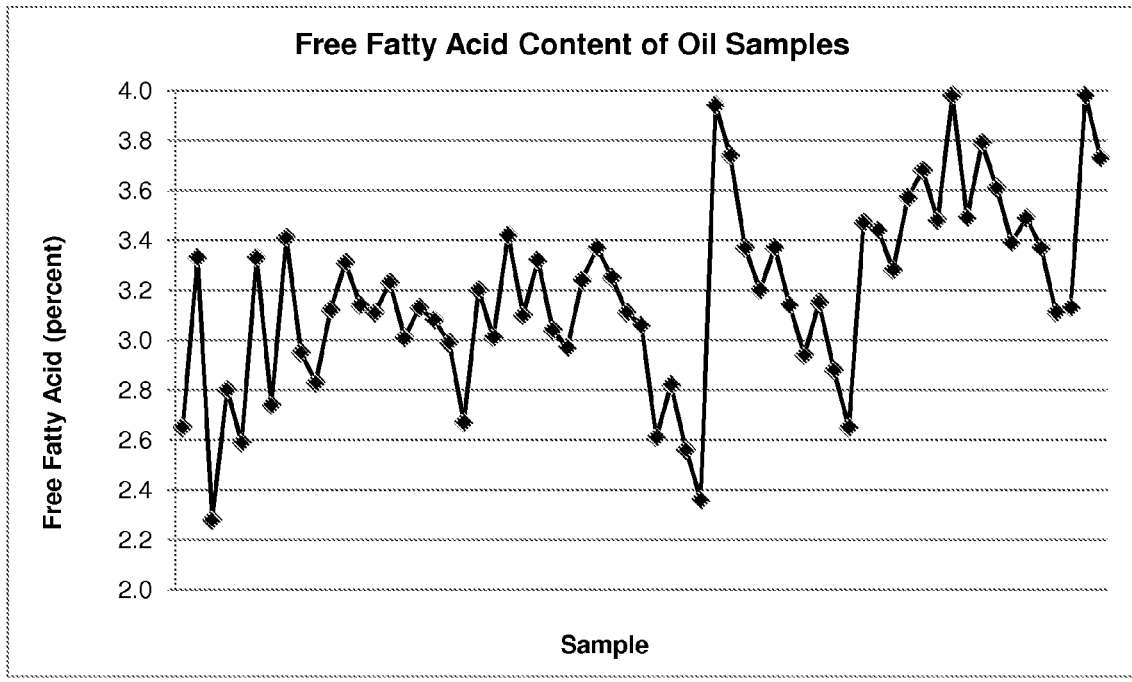
FIG. 9A shows the fatty acid content of the oil samples
FIG. 9B shows the insolubles content of the oil samples
Figure 9C:
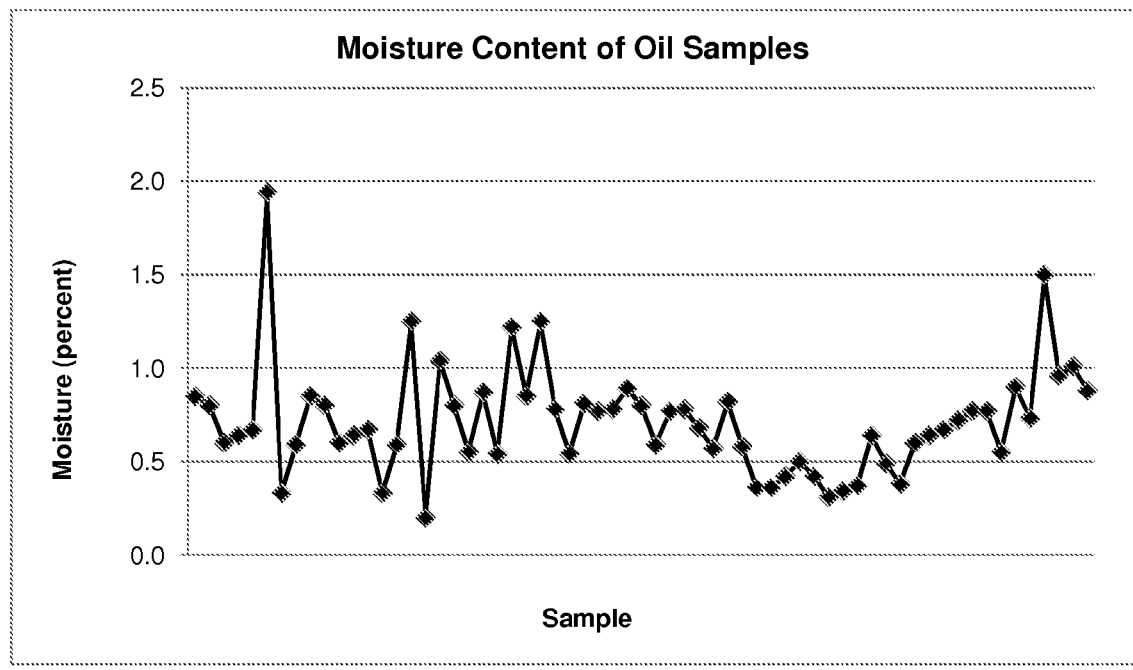
FIG. 9C shows the moisture content of the oil samples
Figure 9D:
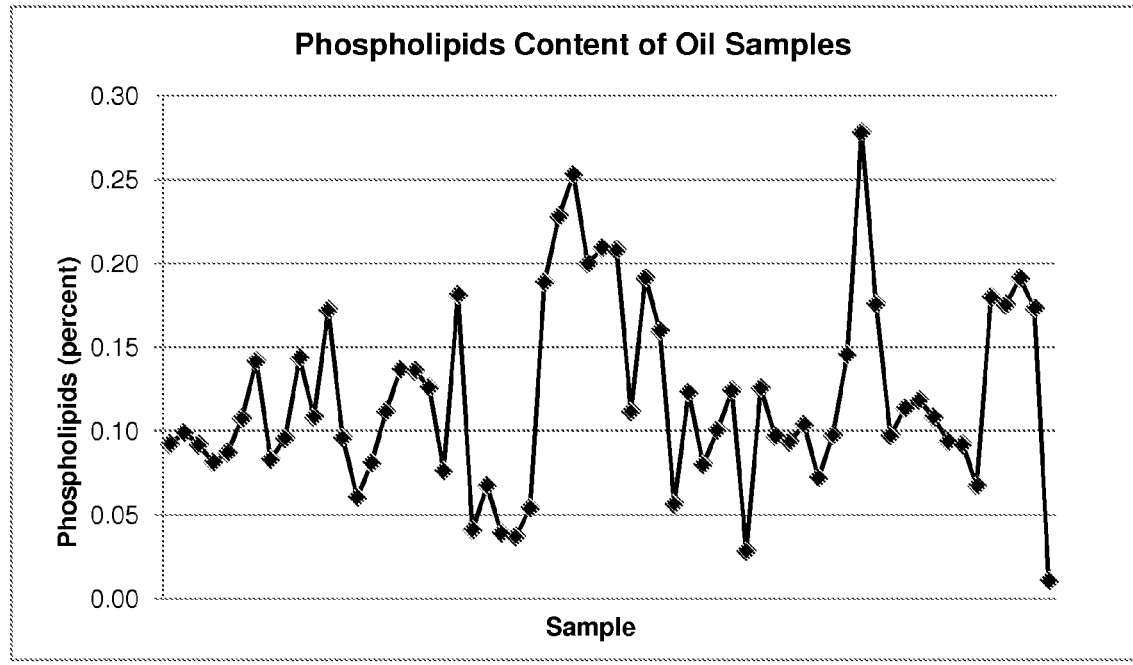
FIG. 9D shows the phospholipids content of the oil samples

Experiments were conducted to determine the amount of free oil present upon adjustment of the oil fraction to various pH levels (FIG. 8). A series of oil fractions, in the form of emulsions samples previously separated by a first application of a centrifugal force were treated with NaOH to adjust the pH to various levels as shown in Table 2. Each sample contained the same amount of oil before adjusting the pH. After adjusting the pH to the targeted value, the volume of free oil was measured.

In summary, the optimum pH was obtained at about 8.2 as evidence by the highest value of free oil volume. The volume of free oil was shown to increase up to this value and then deteriorate thereafter. Thus, an optimum pH for separation exists for each oil fraction sample.

TABLE 2

| | pH | | | | | | | | |
|---|---|---|---|---|---|---|---|---|---|
| | 7.0 | 7.4 | 7.8 | 8.0 | 8.2 | 8.4 | 8.8 | 9.2 | 10.0 |
| Free Fatty Acids (percent) Experiment 1 | 1.0 | 30 | 42 | 45 | 60 | 48 | 50 | 45 | 43 |

Example 3

Experiments were conducted to demonstrate that the combination of adjusting the pH and applying a centrifugal force resulted in (a) higher quality corn oil compositions and (b) higher corn oil composition yield compared to those oil compositions obtained upon application of a centrifugal force alone (FIGS. 9A, 9B, 9C and 9D). The free fatty acid content was shown to be reduced by up to 3% by adjusting the pH in combination with centrifugal force as opposed to centrifugal force alone. The yield of separated oil composition was increased by 140%. The experiment was run for about 30 days, and includes 3 daily samples.

A compositional analysis of the products obtained from one embodiment of the system was performed. The results are summarized in Table 3. The syrup fraction obtained from the ethanol production process was centrifuged to separate into a light fraction (emulsified oil) and a heavy fraction (stickwater). The syrup obtained was mostly free of oil. The heavy fraction was returned to the normal process to be further evaporated and added to wet cake and dried.

The pH of the light fraction was raised to approximately 8.2 from a pH of approximately 3.5. The pH adjusted emulsified material was fed to a second centrifuge step. The heavy fraction (soapstock) from the second centrifuge step was high in soaps and proteins and was mixed with the stickwater and added to the wet cake and dried. The light fraction from the second centrifuge was oil. The oil exhibited a high quality and low free fatty acid content (see FIG. 9A), insolubles (see FIG. 9B), moisture (see FIG. 9C), phospholipids (see FIG. 9D) and unsaponifiables. The oil provided an excellent feedstock for biodiesel production and could be used in food applications with further refining. The distiller's dried grains composition projected to result from the combination of wet cake, soapstock, and low fat syrup exhibited lower fat and higher protein than typical for distillers dried grain.

TABLE 3

| | Fat (percent) | Protein (percent) | Moisture (percent) | Other (percent)*** |
|---|---|---|---|---|
| Starting Material* | 5.4 | 4.1 | 80 | 10 |
| First Light Fraction (Emulsified Oil)* | 35 | 3.6 | 55 | 6.8 |
| First Heavy Fraction (Stickwater)* | 3.5 | 4.2 | 83 | 10 |
| Second Light Fraction (Oil Composition)* | 98 | 0.0 | 0.8 | 1.6 |
| Second Heavy Fraction (Soapstock)* | 5.5 | 5.9 | 77 | 11 |
| Low Fat DDGS** | 4.0 | 30 | 8.7 | 57 |

*= Sampled,
**= Projected,
***= Includes fiber, ash, starch, etc.

Example 4

In a conventional dry-grind ethanol process, whole corn is ground to a flour, mixed with water and cooked at a high temperature to gelatinize the starch and to make it more available for subsequent liquefaction and saccharification by enzymes. The cooked mash is then cooled to facilitate fermentation of the sugars into ethanol. The resulting beer includes soluble and insoluble components, such as proteins, oil, fiber, residual starch and glycerol. The beer is separated into ethanol and whole stillage in distillation. The whole stillage can be dewatered to produce wet cake by removing a thin stillage component by centrifugation. The oil partitions fairly equally, by weight, between thin stillage and the wet cake. Thin stillage is typically further evaporated into syrup, which can be added back onto the wet cake during a drying process that produces distillers dried grains with solubles (i.e. DDGS). Corn oil can be recovered from the syrup by a simple centrifuging step, as described for example in a U.S. patent to GS Cleantech Corporation (U.S. Pat. Ser. No. 7,601,858).

Some dry-grind ethanol processing facilities utilize a modified dry grind process known as raw starch ethanol production. In these facilities, the corn is ground to fine flour, mixed with water and enzymes, and fermented to ethanol-containing beer in a simultaneous saccharification and fermentation reaction. The rest of the raw starch process is similar to the conventional process. However, in the raw starch process the oil cannot be separated from the syrup by a simple centrifugation step, but requires an additional treatment step (pH adjustment) and a second centrifugation step to recover the oil. Overall, raw starch ethanol production requires less energy and cooling water.

Oil extracted from corn DDGS using solvents, and oil extracted centrifugally from thin stillage have been characterized. These oils have similar, or slightly lower concentrations of tocopherols than corn germ oil, but have higher concentrations of phytosterols, tocotrienols, and steryl ferulates, than corn germ oil. However, the oils also tend to have high free fatty acid composition, which is detrimental to biodiesel production as well as to oxidative stability. The ethanol plants supplying the distillers grains for oil extraction in the aforementioned studies were all running the conventional dry-grind ethanol process. To our knowledge, oil extracted from distillers grains from the raw starch ethanol process hasn't been characterized. The oxidative stability of post-fermentation corn oil has not been studied either.

The present example provides the following: 1. To compare the fatty acid and phytochemical composition of oils extracted from corn germ, thin stillage, and DDGS; 2. Evaluate and compare the oxidative stability of these oils; and 3. Determine the oxidative stability of oil extracted from thin stillage at room temperature.

Materials and Methods:
Chemicals

Dry chemicals (ACS grade or better) were obtained from Sigma-Supelco (St. Louis, Mo.) unless otherwise noted in referenced methods. Solvents were HPLC grade and were obtained from Fisher (Fairlawn, N.J.).

Oils

The five oils that were characterized included hexane Soxhlet extracts of corn germ (CG) and DDGS (DDGS), and three oils that were centrifugally extracted from dry grind ethanol production facilities (CS-1, CS-2, CS-3). The corn germ was obtained from an ethanol production facility that operates a dry fractionation process where the corn kernels are separated into germ, fiber, and endosperm fractions prior to fermentation. Corn DDGS was obtained from a raw starch ethanol production facility operated by POET, LLC (Sioux Falls, S.D.). CG and DDGS were extracted overnight (~20 hr) by Soxhlet extraction using hexane. Four parallel Soxhlet extractors with ~100 g/thimble were used several days in a row and the extracts were combined to obtain enough oil from the germ and DDGS for analyses and storage studies. Hexane was removed by rotary evaporation at 40° C., oil was then stirred for 4 hr under a high vacuum to remove any excess hexane, after which the oil was put into several amber bottles, topped with argon to prevent lipid oxidation, and frozen at −20° C. until used for analyses. CS-1 was obtained from a conventional dry grind ethanol plant. CS-2 and CS-3 were obtained from two different production runs from a raw starch ethanol production facility operated by POET. CS-1, CS-2, and CS-3 were shipped overnight, on dry ice, to the research location, and immediately transferred to glass bottles, topped with argon, and frozen (−20° C.) until used for analyses.

Oil Analysis
Acid Value

Acid Value was determined by titration using AOCS official method Cd 3d-63 (AOCS, 1998). The acid value was used to calculate the percent free fatty acids (FFA) as percent oleic acid by dividing the acid value by 1.99 as stated in the method. Each oil was analyzed in triplicate for Acid Value and the mean is reported.

Fatty Acid Composition and Iodine Value

Oil triacylglycerols were transesterified using the method described by Ichihara (1996). Fatty acid methyl esters were analyzed in triplicate by GC as previously described (Winkler and Warner, 2008). The Iodine Values were calculated based on the fatty acid composition according to the AOCS Method Cd 1c-85 (AOCS, 1998).

Tocopherols, Phytosterols, and Steryl Ferulate Analysis

The contents of tocopherols, tocotrienols, and steryl ferulates were analyzed in triplicate in the crude oils by HPLC with a combination of UV and fluorescence detection as previously described (Winkler et al., 2007). In order to analyze total phytosterol content and composition, the oils were saponified, and the phytosterols were extracted and derivatized as previously described (Winkler et al., 2007). Phytosterols were quantitated by GC as described by Winkler and Vaughn (2009). The identity of phytosterol peaks was confirmed by GC-MS analysis performed on an Agilent (Santa Clara, Calif., USA) 6890 GC-MS equipped with a HP-5MS capillary column (30 m 9 0.25 mm 9 0.25 lm), a 5973 mass selective detector, and an 7683 autosampler. The transfer line from GC to the MSD was set to 280° C. The injector and oven temperature programs were the same as described above for the GC-FID instrument. MSD parameters were as follows: scan mode, 50-600 amu, ionizing voltage, 70 eV, and EM voltage, 1,823 V. Mass spectral identification was performed using the Wiley MS database combined with comparison to literature values for relative RT (compared to β-sitosterol) and mass spectra (Beveridge et al., 2002).

Carotenoid Analysis

Carotenoid analysis and quantitation were conducted by HPLC as described by Winkler and Vaughn (2009).

Oxidative Stability Index

The OSI at 110° C. was determined in triplicate following the AOCS Official Method Cd 12b-92 (AOCS, 1998). A Metrohm (Herisau, Switzerland) 743 Rancimat with software control automatically controlled air flow and temperature and calculated the OSI values based on induction time.

Accelerated Storage Study

The study protocol followed AOCS Recommended Practice Cg 5-97 (AOCS, 1998). Oil samples (5 g) were weighed into 40-ml amber glass vials which were loosely capped. For each treatment and day, triplicate vials were prepared. Vials were stored in completely randomized order in a dark oven held at 40±1° C. For each oil, three vials were removed on days one through six and on day eight. CG oil samples were also removed on days 10 and 12. However, as the study progressed, it was determined that the DDGS and CS-2 oils were oxidizing more slowly than the CG oil, so samples were removed on days 12 and 14 order to extend their storage by two more days. Upon removal from the oven, vials were immediately topped with argon, tightly capped, and frozen (−20° C.) until analysis. Analyses were conducted either on the same day or within 2 days of removal from the oven. Peroxide values were determined using the method described by Shantha and Decker (1994). Each oil replicate from the storage studies was analyzed in duplicate. Hexanal in the oil headspace of each replicate was quantified in duplicate by solid-phase microextraction (SPME) and GC analysis as described by Winkler and Vaughn (2009).

Room Temperature Storage Study

CS-2 oil was placed into three, 4L amber bottles. Each bottle was filled to the same volume level of 3.4 L. The amount of headspace above the oil samples amounted to 0.9 L. Bottles were tightly capped and stored in the dark at 20° C.±3° C., the temperature was monitored daily and the high and low temperature was recorded. Samples were taken once a week for 13 weeks. To sample, bottles were first gently shaken for 30 s to mix the contents. Then a glass pipet was inserted into the center of the bottle and 5 ml oil was taken and placed into a screw cap vial, covered with argon, and frozen (−20° C.) until analysis. Peroxide value and headspace analysis of hexanal were performed on the oil samples as described above, and were typically run on the same day or within 1-2 days of sampling.

Results

Fatty Acid Composition and Free Fatty Acids

The fatty acid compositions (Table 4) of all five oils were typical for corn oil. The Iodine Values ranged from 122.4 to 124.3. These results concur with other reports that the fatty acid composition of oil extracted from DDGS and thin stillage are similar to corn oil. The two oils (CS-1 and CS-2) that were centrifugally extracted from syrup from the raw starch ethanol production facilities had the lowest % FFA (2.03% and 2.48%, respectively). The oil recovered by centrifugation of syrup from the traditional dry grind ethanol production plant had the highest Acid Value, with 10.1% FFA. Other studies have reported FFA content of oil recovered by centrifugation of thin stillage ranging from 11.2-16.4%. These results indicate that the elimination of the cooking step in the raw starch process reduces the production of FFA. The oil extracted from DDGS using hexane had the second highest acid value (7.42% FFA). Winkler-Moser and Vaughn (*J. Am. Oil Chem. Soc.*, 2009, 86, 1073-1082) reported FFA content of 6.8% (w/w) in hexane Soxhlet extracted DDGS oil, while Moreau et al. (*J. Am. Oil Chem. Soc.*, 2010b, In Press) reported FFA content ranging from 8-12% in DDGS that was extracted with hexane using accelerated solvent extraction. FFA content of DDGS extracts has been shown to vary widely depending on the extraction method and conditions and on the solvent used. The DDGS used in this study also came from a raw starch ethanol plant, so it might be expected to have lower FFA. However, high temperatures used to dry the wet grains may have contributed to the increase in FFA. In one experiment, Moreau et al. (*J. Am. Oil Chem. Soc.*, 2010b, In Press) demonstrated that oil extracted from thin stillage and distillers dried grains (prior to mixing the grains with the syrup) had high FFA content that carried through to the DDGS. The FFA content of hexane extracted corn germ was 3.8%, which is slightly higher than the average of 2.5% FFA typically found in crude corn germ oil. For biodiesel production, oil with an Acid Value greater than one requires pretreatment because the free fatty acids form soaps during base-catalyzed esterification, which interfere with the separation of the glycerol from the fatty acid methyl esters. Thus, crude oils with lower free fatty acids will have lower oil loss due to the pre-treatment. Free fatty acids decrease the oxidative stability of oils and can also precipitate at ambient temperatures, both of which could negatively impact fuel performance.

Content and Composition of Tocopherols, Tocotrienols, and Carotenoids

Tocopherols are common in vegetable oils and are the primary antioxidants protecting most oils. With corn and other plants, the tocopherol and tocotrienol content will vary based upon factors including hybrid, growth conditions, post-harvesting and processing conditions, as well as the type of solvent used for extraction. Therefore, in this study little can be inferred about how processing practices affected tocopherol levels since each production facility and even each production run will have started with different batches of whole corn. Gamma- and alpha-tocopherol were the most prominent homologues detected in all five oils (Table 5), along with a small amount of delta-tocopherol, which is the typical tocopherol profile for corn oil. CG oil had the highest total concentration of tocopherols (1433.6 μg/g oil) followed by the hexane extracted DDGS (1104.2). The levels in the DDGS oil are similar to what was previously reported in hexane extracted DDGS from a conventional dry grind production facility. Tocopherols in corn are localized in the germ portion of the kernel, so the rest of the corn kernel contributes little to the tocopherol content. CS-1, CS-2, and CS-3 were all lower in alpha-tocopherol compared to CG and DDGS oils, but were similar to levels reported in oil extracted centrifugally from thin stillage (Moreau et al., *J. Am. Oil Chem. Soc.*, 2010a, In Press).

TABLE 5

Content of tocols and carotenoids, and the oxidative stability index (OSI) at 110° C., for oils extracted from corn germ (CG), distillers dried grains with solubles (DDGS), and centrifugally extracted thin stillage syrup (CS-1, CS-2, CS-3)

|  | CG | DDGS | CS-1 | CS-2 | CS-3 |
| --- | --- | --- | --- | --- | --- |
| Total Tocopherols (μg/g) | 1433.6 | 1104.2 | 1056.9 | 931.3 | 783.4 |
| Alpha-tocopherol | 213.8 | 295.6 | 164.5 | 160.4 | 123.2 |
| Gamma-tocopherol | 1185.4 | 760.8 | 852.7 | 742.0 | 640.0 |
| Delta-tocopherol | 34.3 | 47.8 | 39.7 | 28.8 | 20.2 |
| Total Tocotrienols (μg/g) | 235.6 | 1762.3 | 1419.6 | 1224.4 | 1175.2 |
| Alpha-tocotrienol | 21.9 | 471.9 | 328.5 | 243.6 | 269.4 |
| Gamma-tocotrienol | 165.6 | 1210.0 | 1063.6 | 963.4 | 880 |
| Delta-tocotrienol | 48.1 | 80.3 | 27.5 | 17.3 | 25.8 |
| Total Carotenoids (μg/g) | 1.33 | 75.02 | 129.48 | 61.1 | 85.0 |
| Lutein | 0.37 | 46.69 | 75.69 | 38.13 | 53.7 |
| Zeaxanthin | 0.4 | 24.16 | 45.58 | 16.78 | 23.7 |
| Beta-cryptoxanthin | 0.56 | 3.31 | 7.35 | 4.12 | 5.1 |
| Beta-carotene | ND[a] | 0.86 | 0.86 | 2.07 | 2.5 |
| OSI (hr) | 3.91 | 6.62 | 4.45 | 4.52 | 5.27 |

[a]Not detected

TABLE 4

Acid value, fatty acid composition, and calculated Iodine Value of oils extracted from corn germ (CG), distillers dried grains with soluble (DDGS), and centrifugally extracted thin stillage syrup (CS-1, CS-2, CS-3)

|  | CG | DDGS | CS-1 | CS-2 | CS-3 |
| --- | --- | --- | --- | --- | --- |
| Acid Value (mg KOH/g) | 10.7 ± 0.07 | 20.8 ± 0.36 | 28.3 ± 0.32 | 5.70 ± 0.13 | 6.88 ± 0.09 |
| FFA (% oleic acid) | 3.80 ± 0.03 | 7.42 ± 0.13 | 10.1 ± 0.11 | 2.03 ± 0.05 | 2.48 ± 0.05 |
| Fatty Acid Composition (%) |  |  |  |  |  |
| 16:0 | 13.1 | 12.9 | 11.5 | 12.2 | 12.9 |
| 16:1 | 0.0 | 0.1 | 0.1 | 0.1 | 0.1 |
| 18:0 | 1.5 | 1.8 | 1.7 | 1.8 | 1.5 |
| 18:1 | 29.2 | 28.1 | 29.3 | 28.3 | 27.5 |
| 18:2 | 55.0 | 55.5 | 55.6 | 55.3 | 55.9 |
| 20:0 | 0.2 | 0.3 | 0.3 | 0.4 | 0.3 |
| 18:3 | 1.0 | 1.2 | 1.17 | 1.2 | 1.2 |
| 20:1 | 0.0 | 0.0 | 0.2 | 0.3 | 0.2 |
| Calculated Iodine Value | 122.4 | 123.1 | 124.3 | 123.7 | 124.1 |

Tocotrienols are common in rice bran oil and palm oil, but are not abundant in most commercial vegetable oils. Their antioxidant activity is similar to tocopherols in bulk oil systems, but they also appear to have hypocholesterolemic, anti-cancer, and neuroprotective properties. The post-fermentation corn oils (DDGS, CS-1, CS-2, and CS-3) were higher in tocotrienol concentration compared to CG oil, because tocotrienols are found in the endosperm fractions, which are mostly removed during the fractionation of corn germ. Thus, despite having lower tocopherol concentration, all of the post-fermentation oils were higher in total tocol concentration compared to the CG oil.

The post-fermentation corn oils were much higher in carotenoids than the extracted corn germ oil as well. However, the concentration of carotenoids was substantially lower than the tocols in five oils (Table 5). As with tocotrienols, carotenoids are localized to the endosperm fraction of corn kernels. The main carotenoids in the oils were lutein and zeaxanthin, as well as lower quantities of beta-cryptoxanthin and beta-carotene. Carotenoid content and composition were similar to amounts found in DDGS oil in a previous study, however, Moreau et al. (J. Am. Oil Chem. Soc., 2010a, In Press) reported carotenoid content in centrifugally extracted thin stillage oil ranging from 295 to 405 µg/g oil. Carotenoids are substantially affected by corn hybrid, which may explain the discrepancy. Beta-carotene and beta-cryptoxanthin are both precursors to Vitamin A, while lutein and zeaxanthin are both protective against age-related macular degeneration and cataracts. Carotenoids have also been shown to have a number of beneficial physiological actions other than Vitamin A activity, including antioxidant activity, enhanced immune response, and chemoprotective activity against several types of cancer.

Content and Composition of Phytosterols

The content of total phytosterols in the three oils ranged from 1.5-2.0% (w/w) (Table 6). The post-fermentation corn oils were higher in total phytosterols compared to the CG oil because they include phytosterols and ferulate phytosterol esters from the bran and pericarp, in addition to the phytosterols from the germ portion of the corn kernel. The phytosterol composition is also different between CG oil and the post-fermentation corn oils. DDGS and CS-1, CS-2, and CS-3 oils had similar concentrations of the common phytosterols campesterol, stigmasterol, and sitosterol compared to CG oil. However, they had a much higher concentration of the two saturated phytosterols (phytostanols), campestanol and sitostanol. The high content of these phytostanols is due to their preferential esterification, in corn, to steryl ferulates, the contents of which are also shown in Table 6. Steryl ferulates are found in the inner pericarp of corn and other grains. The presence of a small amount of these compounds in the corn germ oil indicates that there may have been some contamination of the germ by some inner pericarp tissue, as it has been established that these compounds are unique to the aleurone layer of the pericarp. Phytosterols are highly valued as ingredients in functional foods due to their ability to lower blood cholesterol by blocking re-adsorption of cholesterol from the gut. Steryl ferulates have been shown to retain the cholesterol lowering ability of phytosterols, and also have antioxidant activity due to the ferulic acid moiety.

TABLE 6

Content and composition of phytosterols in oils extracted from corn germ (CG), distillers dried grains with solubles (DDGS), and centrifugally extracted thin stillage syrup (CS-1, CS-2, CS-3).

|  | CG |  | DDGS |  | CS-1 |  | CS-2 |  | CS-3 |  |
| --- | --- | --- | --- | --- | --- | --- | --- | --- | --- | --- |
|  | mg/g | %[a] | mg/g | % | mg/g | % | mg/g | % | mg/g | % |
| Total Phytosterols | 14.9 |  | 21.7 |  | 18.7 |  | 20.1 |  | 20.2 |  |
| Campesterol | 3.08 | 20.7 | 2.97 | 13.7 | 2.74 | 14.7 | 2.74 | 13.6 | 3.0 | 14.7 |
| Campestanol | 0.25 | 1.7 | 1.35 | 6.2 | 1.40 | 7.5 | 1.30 | 6.5 | 1.4 | 6.7 |
| Stigmasterol | 0.98 | 6.6 | 1.10 | 5.1 | 0.76 | 4.1 | 0.91 | 4.5 | 0.89 | 4.4 |
| Sitosterol | 9.04 | 60.9 | 10.3 | 47.5 | 8.77 | 46.9 | 9.36 | 46.5 | 9.3 | 46.1 |
| Sitostanol | 0.66 | 4.4 | 3.72 | 17.2 | 3.59 | 19.2 | 3.45 | 17.2 | 3.2 | 16.0 |
| Avenasterol | 0.54 | 3.7 | 0.93 | 4.3 | 0.86 | 4.6 | 0.94 | 4.7 | 1.0 | 5.2 |
| Cycloartenol | 0.28 | 1.9 | 0.71 | 3.2 | 0.59 | 3.2 | 0.74 | 3.7 | 0.73 | 3.6 |
| 24-methylene cycloartanol | ND[b] | 0 | 0.30 | 1.4 | ND | 0 | 0.34 | 1.7 | 0.30 | 1.5 |
| Citrostadienol | ND | 0 | 0.31 | 1.4 | ND | 0 | 0.31 | 1.6 | 0.36 | 1.8 |
| Steryl Ferulates (mg/g) | 0.58 | 3.9 | 3.42 | 15.7 | 3.15 | 16.8 | 3.38 | 16.8 | 3.35 | 16.6 |

[a]The weight percentage of total phytosterols
[b]Not detected

Oxidative Stability Index (OSI)

The oxidative stability of oils are affected by many factors, including fatty acid composition, concentration and stability of antioxidants in the oil, and the presence of prooxidant compounds, such as free fatty acids, lipid peroxides, or prooxidant metals. The Rancimat is an accelerated test (taking several hours to a day, depending on the oil and test temperature) used to establish the relative oxidative stability of oils, as measured by the induction time (called the oxidative stability index, OSI) for an oil to begin oxidizing under controlled temperature and air flow conditions. The OSI of the CG oil was lowest, while DDGS oil had the highest stability (Table 5), which corresponds to the lowest and the highest concentration of antioxidant tocopherols. CS-1 had a slightly lower OSI than CS-2 and CS-3 despite having a higher concentration of tocols; this may be explained by its higher content of FFA and higher initial peroxide value.

Accelerated Storage Study

Figure 10:
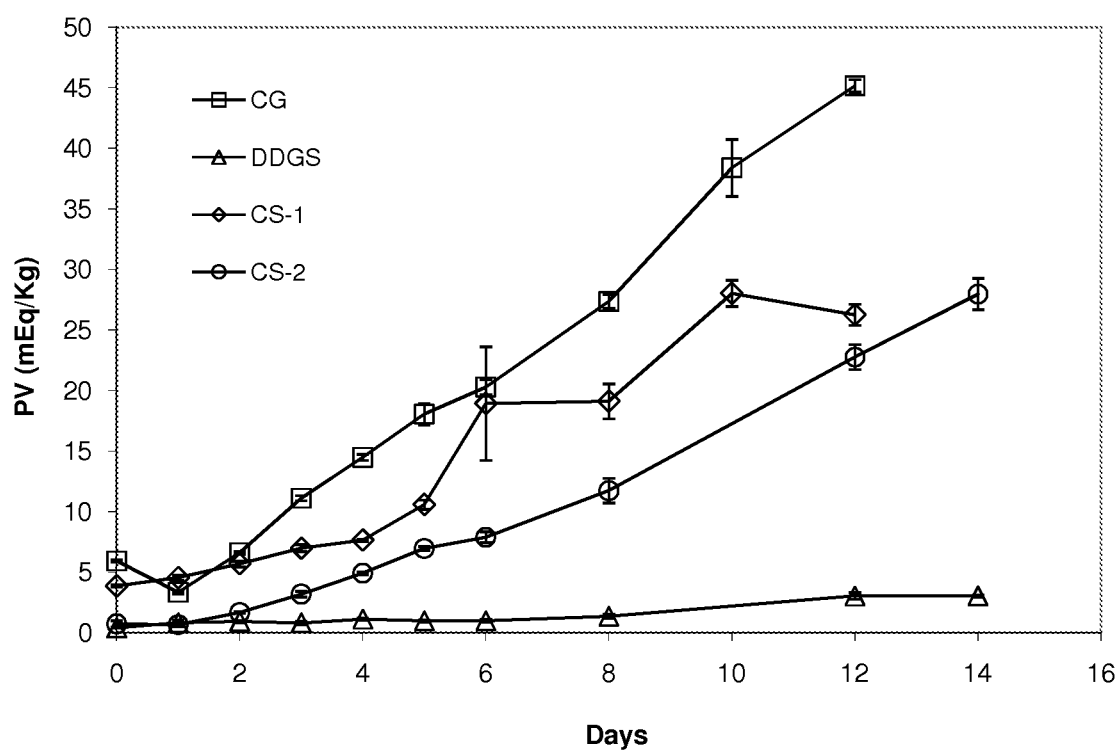
FIG. 10 show the peroxide value of oils stored at 40° C. in the dark.

While the OSI is a quick method for determining relative stability of various oils, it is often recommended that oil stability be measured at lower temperatures as well, since oxidation mechanisms change at higher temperatures. Peroxide value is an indicator of the primary stage of lipid oxidation where lipid radicals are attacked by oxygen to form lipid hydroperoxides. At temperatures lower than 100° C., lipid peroxides accumulate until they begin to break down to form secondary oxidation products including volatile aldehydes (e.g., hexanal), ketones, and esters. The CG oil showed the highest rate of increase in peroxides when stored at 40° C., indicating that it was the most susceptible to oxidation (FIG. 10). CS-1 and CS-2 were more stable than the CG oil, but CS-2 was slightly more stable than CS-1. As a point of comparison, it took CG 2-3 days to reach a peroxide value of 10 mEq/Kg, 5 days for CS-1, and between 6-8 days for CS-2. The hexane extracted DDGS oil was most stable, and did not show any increase in peroxide value for the first 8 days of storage, after which it increased at a slow rate and did not even reach a value of 5 mEq/kg by the end of the study. The trends in relative oxidative stability were the same as predicted by the OSI values, however, the OSI values did not demonstrate as clearly the differences in stability of the four oils as seen in this evaluation at a lower temperature.

Figure 11:
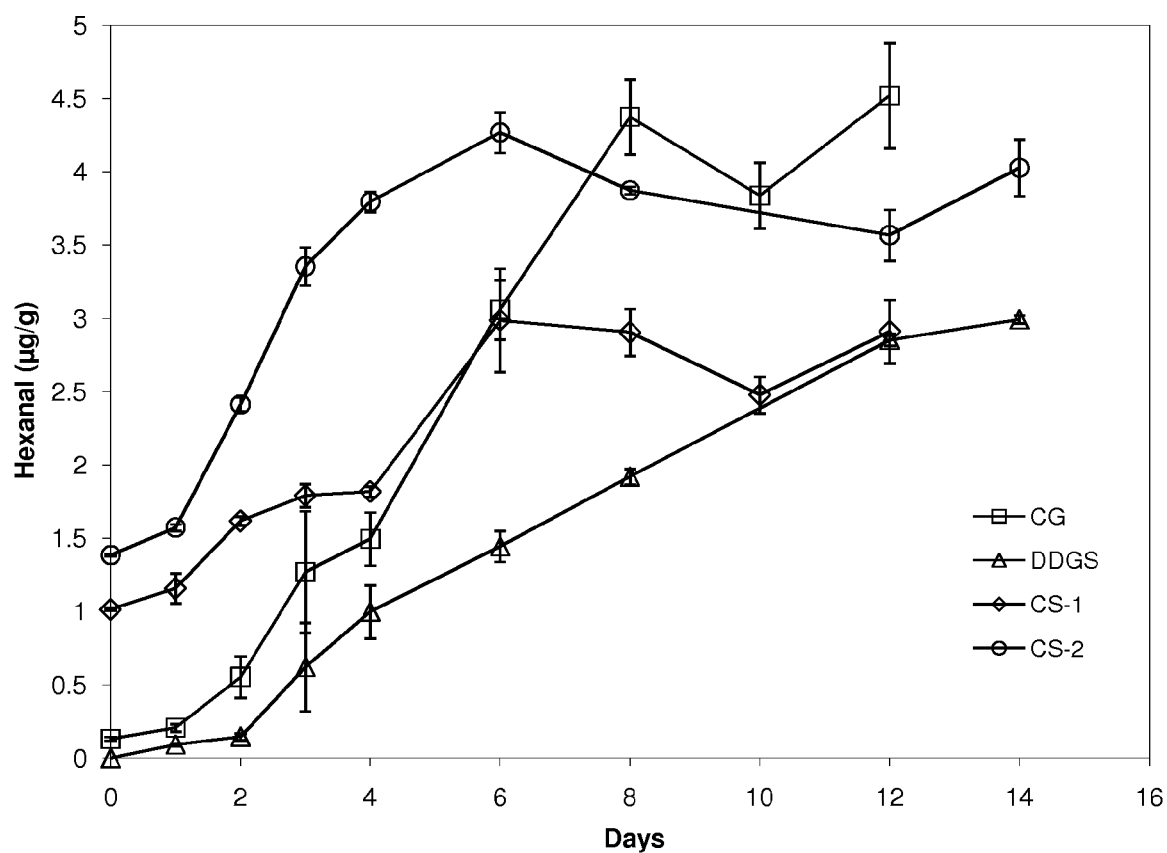
FIG. 11 show the hexanal content of oils stored at 40° C. in the dark.

As lipid hydroperoxides break down, they form volatile compounds that can be measured in the headspace as indicators of secondary lipid oxidation. Hexanal is produced from the 13-hydroperoxide of linoleic acid, and is therefore often used as a reliable indicator of secondary lipid oxidation in oils that are high in linoleic acid. At day 0 of the study, the CG and DDGS oils had very low hexanal content, while CS-1 and CS-2 had about 1-1.4 μg/g hexanal in the oil (FIG. 11). Since the CG and DDGS oils were treated by rotary evaporation to remove hexane after extraction, there may have been residual levels of hexanal (and other volatile compounds) in these oils as well that were removed by the rotoevaporation. The hexanal content increased to 4 μg/g in CG, but leveled off after day 8. In CS-1 and CS-2, hexanal contents increased to 3 μg/g and 4 μg/g, respectively, and also leveled off around 6 days of storage. Hexanal increased at a slower rate in the DDGS oil, to a final level of 3 μg/g. The total hexanal content remained relatively low in all of the oils throughout the storage study, indicating perhaps, that the hexanal that formed during this time period was from the breakdown of residual lipid peroxides already present in the three oils, and that the process of accelerated peroxide breakdown and aldehyde formation had not yet taken place. This is supported by the fact that the peroxide values had not yet leveled off or decreased, as is often seen in storage studies where oil is in the secondary stages of lipid oxidation.

Room Temperature Storage Study

Figure 12:
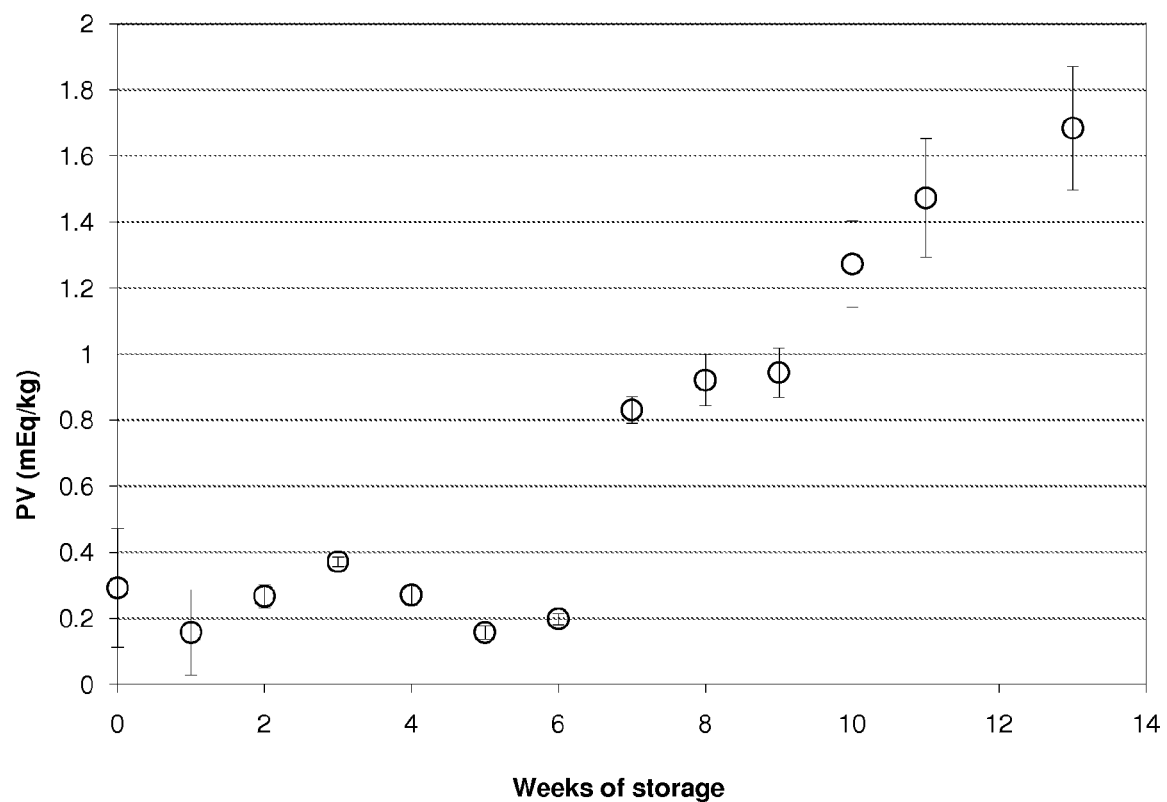
FIG. 12 show the peroxide value of CS-2 oil during storage at 20° C.
Figure 13:
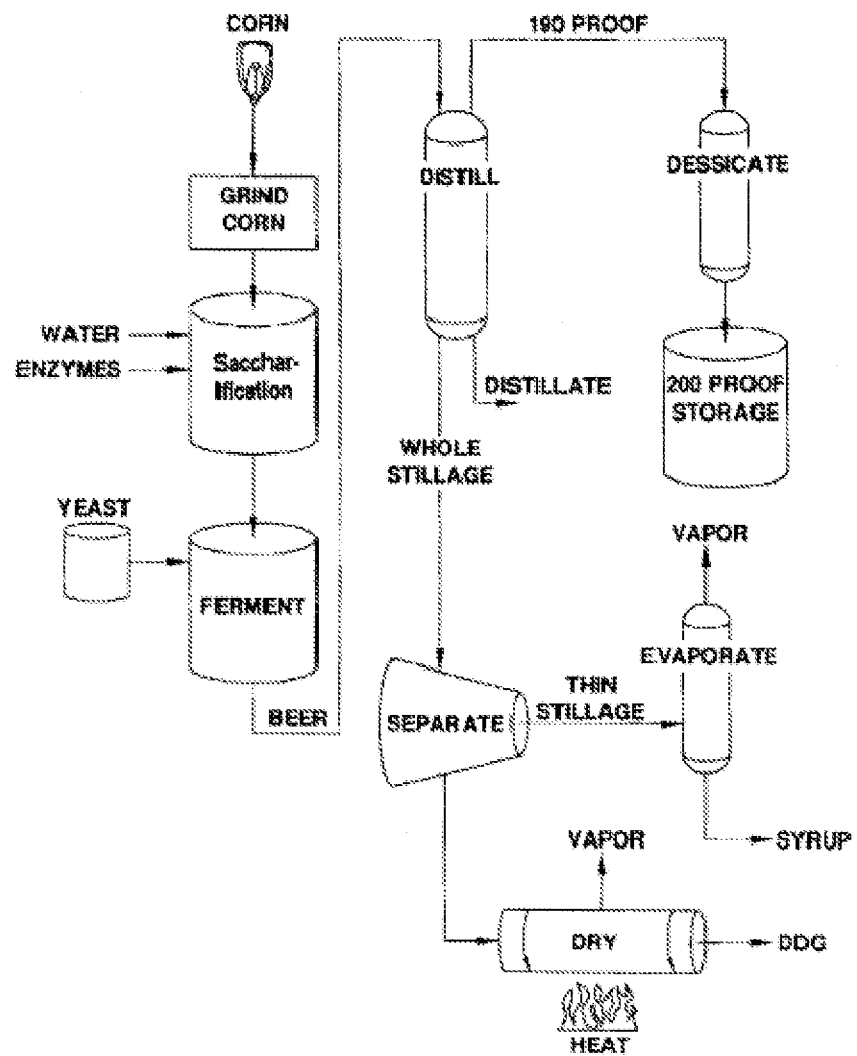
FIG. 13 shows an exemplary process flow diagram.
Figure 14A:
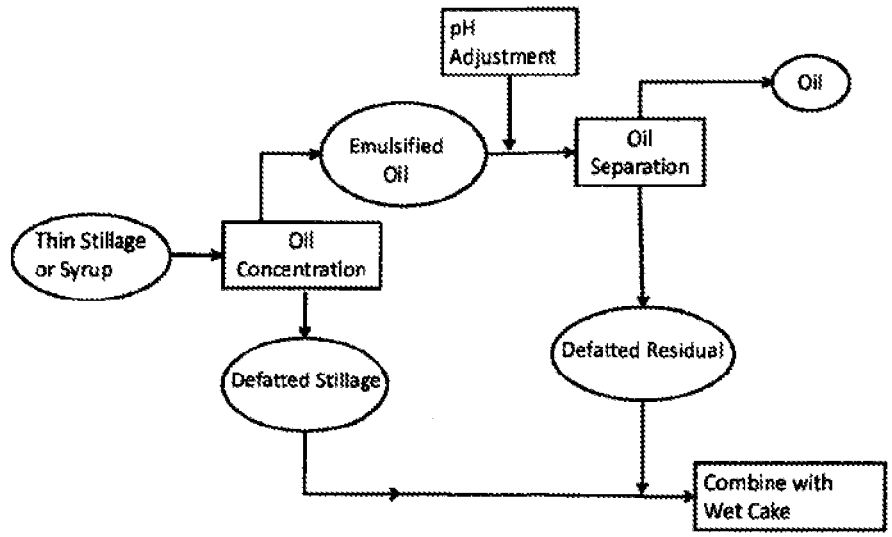
FIGS. 14A, 14B, 14C, 14D and 14E show various flow diagrams for providing the oil composition and the distillers dried grains of the invention.
Figure 14B:
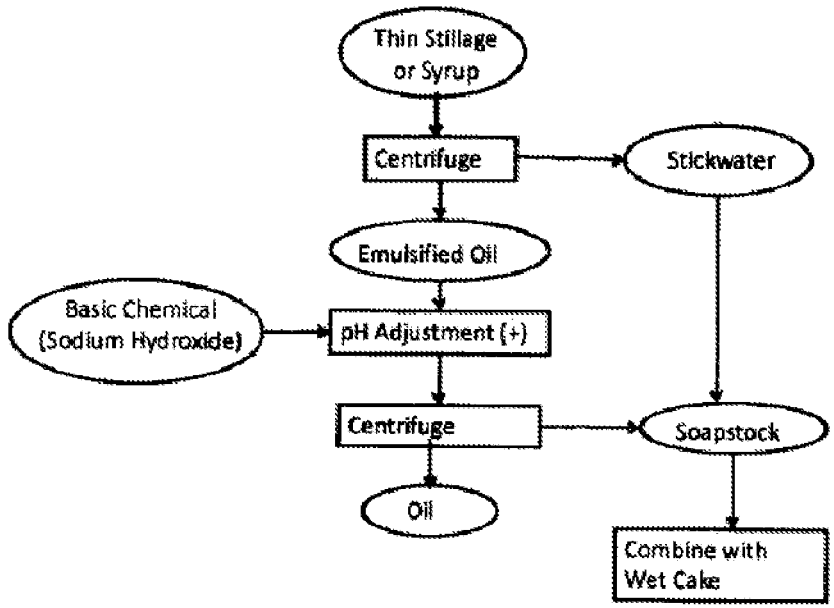
Figure 14C:
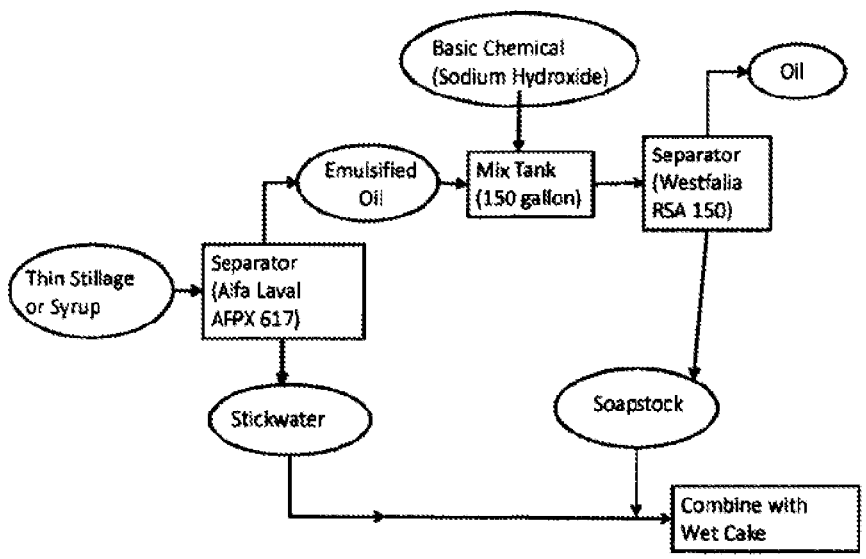
Figure 14D:
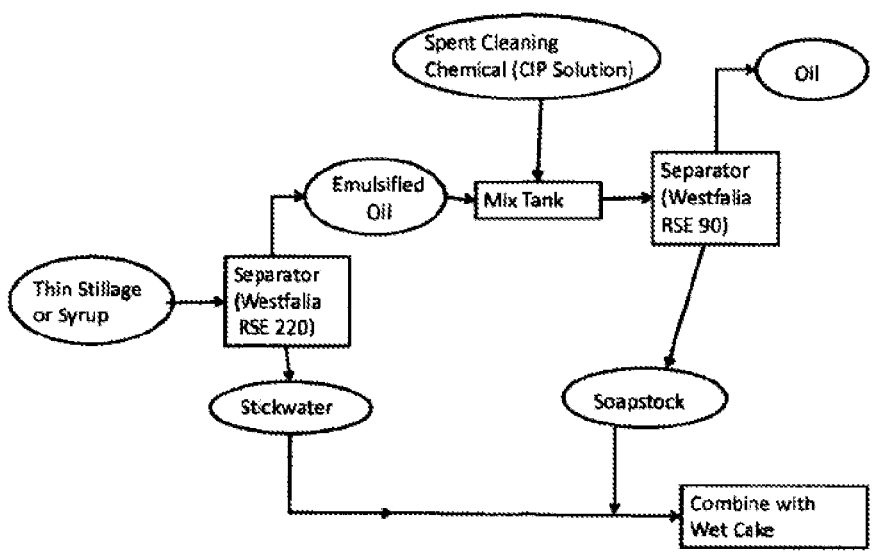
Figure 14E:
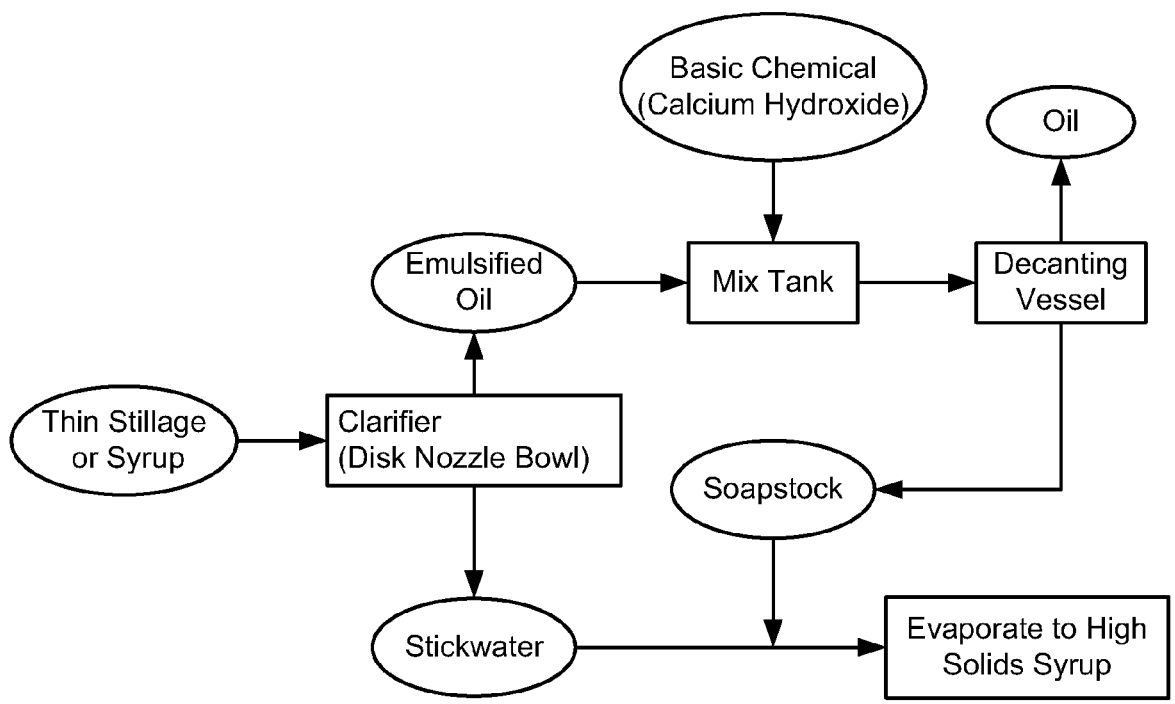

While the OSI and accelerated storage studies are useful for determining the relative stability of oils with differing fatty acid compositions or antioxidant levels, they still cannot be used to predict shelf stability under real life conditions. Accelerated storage studies would need to be performed over at least three different temperatures and the induction periods would have to be plotted in order to predict the induction period at a given temperature. In order for oil derived from the ethanol production process to be used in applications such as biodiesel production, it is of interest to predict its stability during storage. Larger volumes of CS-2 oil were stored in the dark at room temperature and determined PV and hexanal content weekly to determine the induction time under these conditions. There was not enough of the other oils to include them in this portion of the study. The peroxide value remained in a lag stage for 6 weeks, after which time it started to slowly increase (FIG. 12). However, by 13 weeks of storage, it was still below a peroxide value of 2.0 mEq/kg oil. Hexanal content in the headspace was also measured weekly, but content remained the same throughout the study indicating that the oil was still in the primary stages of lipid oxidation by the end of the study. Regression analysis of the oil PV based on the rate of increase after the lag phase ended (weeks 7 through 13) predicted that it would reach a PV of 10 mEq/Kg after approximately 58 weeks of storage under these same conditions. This study could not be used to predict the stability of the oil in commercial production conditions where factors such as the surface area to volume ratio, the use of inert gas in the headspace, and temperature fluctuations would all impact the rate of lipid oxidation. However, the results indicate that under ideal conditions of a low surface area to volume ratio, room temperature, and limited light exposure, crude thin stillage oil would likely remain oxidatively stable for several months or more. This is an important issue for storage and transport of the crude thin stillage oil prior to further processing for biodiesel or other uses.

Conclusions

This Example compared the composition and oxidative stability of oils extracted from corn germ, corn distillers dried grains, and from thin stillage from a conventional dry grind ethanol production facility as well as from a raw starch ethanol production facility. The fatty acid compositions of all five oils were typical for corn oil. Oil extracted from thin stillage in a raw starch production facility has lower FFA than from thin stillage from a conventional dry grind ethanol production facility. This is likely due to lower processing temperatures used in the raw starch process where the cooking stage is eliminated. All of the post-fermentation oils had higher concentrations of tocotrienols, carotenoids, phytosterols, and ferulate phytosterol esters compared to the corn germ oil. The increased concentrations of the antioxidant tocotrienols carotenoids, and steryl ferulates are likely responsible for their increased stability compared to corn germ oil.

Soybean oil is the most common feedstock for biodiesel, but this study indicates that from the standpoint of fatty acid composition and oxidative stability, oil extracted from thin stillage would be an economical alternative. Considering that over 25 million metric tons of DDGS with roughly 10% oil are produced from the ethanol industry each year, enough oil could be recovered to offset a substantial amount of the soybean oil that is directed to biodiesel production. This would result in two fuels, ethanol and biodiesel, produced from a single feedstock.

The embodiments as disclosed and described in the application (including the FIGURES and Examples) are intended to be illustrative and explanatory of this invention. Modifications and variations of the disclosed embodiments, for example, of the apparatus and processes employed (or to be employed) as well as of the compositions and treatments used (or to be used), are possible; all such modifications and variations are intended to be within the scope of this invention.

What is claimed is:

1. A method for providing a corn oil composition having a free fatty acid content of less than about 2 weight percent and being formulated for use as biodiesel from a first aqueous layer constituting a corn fermentation residue, said method comprising the steps of:
   a) obtaining the first aqueous layer from the corn fermentation residue;
   b) adjusting the pH of the first aqueous layer to provide a corn oil layer and a second aqueous layer; and
   c) separating the corn oil layer from the second aqueous layer to provide the corn oil composition having a free fatty acid content of less than about 2%;
   wherein the corn oil composition is formulated for use as biodiesel.

2. The method of claim 1, wherein the first aqueous layer has a moisture content of between about 95% and about 60%.

3. The method of claim 1, wherein the first aqueous layer comprises thin stillage.

4. The method of claim 3, further comprising the step of evaporating the thin stillage prior to the step of adjusting the pH of the first aqueous layer.

5. The method of claim 1, wherein the first aqueous layer comprises syrup.

6. The method of claim 1, wherein the step of adjusting the pH comprises adding a base.

7. The method of claim 1, wherein the step of adjusting the pH comprises adding a base selected from the group consisting of sodium hydroxide, potassium hydroxide, calcium hydroxide, or spent alkali wash solution.

8. The method of claim 1, wherein the pH of the first aqueous layer is less than about 4 prior to the step of adjusting the pH of the first aqueous layer.

9. The method of claim 1, wherein the pH of the first aqueous layer is about 3.5 prior to the step of adjusting the pH of the first aqueous layer.

10. The method of claim 1, wherein the pH of the first aqueous layer is from about 7.5 to about 10 after adjusting the pH of the first aqueous layer.

11. The method of claim 1, wherein the pH of the first aqueous layer is from about 8 to about 9 after adjusting the pH of the first aqueous layer.

12. The method of claim 1, wherein the pH of the first aqueous layer is about 8.2 after adjusting the pH of the first aqueous layer.

13. The method of claim 1, wherein the step of obtaining the first aqueous layer from the corn fermentation residue comprises centrifuging.

14. The method of claim 1, where the step of obtaining the first aqueous layer from the corn fermentation residue comprises the steps of:
 a) separating the first aqueous layer into a water layer and an emulsion layer; and
 b) adjusting the pH of the emulsion layer to provide a corn oil layer and a second aqueous layer.

15. The method of claim 14, wherein the step of obtaining the first aqueous layer from the corn fermentation residue to provide an emulsion layer and a first aqueous layer comprises centrifuging.

16. The method of claim 1, wherein the step of separating the corn oil layer from the second aqueous layer comprises centrifuging.

17. The method of claim 1, wherein the corn oil layer comprises a free fatty acid content of less than about 2 weight percent.

18. The method of claim 1, wherein the corn oil layer comprises a moisture content of from about 0.2 to about 1 weight percent.

19. The method of claim 1, wherein the corn oil layer comprises an alkali metal ion and/or alkaline metal ion content of greater than 10 parts per million.

20. The method of claim 1, wherein the corn oil layer has an insoluble content of less than about 1 weight percent.

21. The method of claim 1, wherein the corn oil layer exhibits a peroxide value of less than about 2 parts per million.

22. The method of claim 1, wherein the corn oil layer exhibits an oxidative stability of greater than about 4 hours at a temperature of about 110° C.

* * * * *